(12) United States Patent
Mattingly et al.

(10) Patent No.: US 7,906,293 B2
(45) Date of Patent: Mar. 15, 2011

(54) ACRIDINIUM PHENYL ESTERS USEFUL IN THE ANALYSIS OF BIOLOGICAL

(75) Inventors: Phillip G. Mattingly, Third Lake, IL (US); Maciej Adamczyk, Gurnee, IL (US); Roy Jeffrey Brashear, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 380 days.

(21) Appl. No.: 11/697,835

(22) Filed: Apr. 9, 2007

(65) Prior Publication Data

US 2008/0248493 A1 Oct. 9, 2008

(51) Int. Cl.
G01N 33/53 (2006.01)
(52) U.S. Cl. .......................................... 435/7.1; 436/546
(58) Field of Classification Search ........................ None
See application file for complete search history.

(56) References Cited

U.S. PATENT DOCUMENTS

| 5,241,070 | A | 8/1993 | Law et al. |
|---|---|---|---|
| 5,340,714 | A | 8/1994 | Katsilometes |
| 5,491,072 | A | 2/1996 | Akhavan-Tafti et al. |
| 5,523,212 | A | 6/1996 | Akhavan-Tafti et al. |
| 5,593,845 | A | 1/1997 | Akhavan-Tafti et al. |
| 5,670,644 | A | 9/1997 | Akhavan-Tafti et al. |
| 5,723,295 | A | 3/1998 | Akhavan-Tafti et al. |
| 5,750,698 | A | 5/1998 | Akhavan-Tafti et al. |
| 6,673,560 | B1 | 1/2004 | Sharpe et al. |
| 2002/0177240 | A1* | 11/2002 | Kundu ............................ 436/518 |
| 2003/0232405 | A1* | 12/2003 | Akhavan-Tafti et al. ........ 435/25 |
| 2008/0199973 | A1* | 8/2008 | Evangelista et al. ........... 436/536 |

FOREIGN PATENT DOCUMENTS

| EP | 0 625 510 A2 | 11/1994 |
|---|---|---|
| EP | 0 750 748 B1 | 5/2001 |
| EP | 0 778 946 B1 | 10/2002 |
| EP | 0 625 510 B1 | 4/2003 |
| WO | WO 93/23756 A1 | 11/1993 |
| WO | WO 94/26927 A1 | 11/1994 |
| WO | WO 95/23971 A1 | 9/1995 |
| WO | WO 95/28495 A1 | 10/1995 |
| WO | 9529255 | 11/1995 |
| WO | WO 96/07912 A1 | 3/1996 |
| WO | 0031543 | 6/2000 |
| WO | WO 2005/005385 A1 | 1/2005 |
| WO | WO 2005/015214 A1 | 2/2005 |
| WO | WO 2005/015215 A1 | 2/2005 |
| WO | 20060130736 | 12/2006 |

OTHER PUBLICATIONS

Adamczyk, et al., Analytica Chimica Acta, "Homogeneous chemiluminescent assays for free choline in human plasma and whole blood", 579, 61-67 (2006).

Adamczyk, et al., Bioorganic & Medicinal Chemistry Letters, "Rapid high-throughput detection of peroxide with and acridinium-9carboxamide: Ahomogeneous chemiluminescent assay for plasma choline", In Press (2006).

Brown, et al., Analytical Biochemistry, "Employment of a Phenoxy-Substituted Acridinium Ester as a Long-Lived Chemiluminescent Indicator of Glucose Oxidase Activity and Its Application in an Alkaline Phosphatase Amplification Cascade Immunoassay", 256, 142-151 (1998).

McCapra, et al., Photochemistry and Photobiology, "Chemiluminescence Involving Peroxide Decompositions", 4, 1111-1121 (1965).

Razavi, et al., Luminescence, Stable and versatile active acridinium esters I, 15, 239-244 (2000).

Razavi, et al., Luminescence, Stable and versatile active acridinium esters II, 15, 245-249 (2000).

de Silva, et al., 13th Int. Symposium on Bioluminescence and Chemiluminescence, Symposium Abstract. "Use of new chemiluminescent reagent in detection of oxidasse enzymes and their substrates by a coupled enzyme reaction", Aug. 2-6, 2004 Yokohama, Japan.

de Silva, et al., 13th Int. Symposium on Bioluminescence and Chemiluminescence, "Use of New Chemiluminescent Reagent in Detection of Oxidase Enzymes and Their Substrates by a Coupled Enzyme Reaction", Aug. 2-6, 2004 Yokohama, Japan, Published on website of Lumigen Inc. on Jun. 7, 2006, pp. 1-10.

Waldrop III, et al., Luminescence, "Chemiluminescent determination of hydrogen peroxide with 9-acridinecarbonylimidazole and use in measurement of glucose oxidase and alkaline phosphatase activity" 15, 169-182 (2000).

ISA/US, International Search Report (Search Completed Jul. 2, 2008), International Application PCT/US2008/59710.

* cited by examiner

*Primary Examiner* — Jacob Cheu

(74) *Attorney, Agent, or Firm* — Audrey L. Bartnicki; Lisa V. Mueller; Polsinelli Shughart

(57) ABSTRACT

The present invention relates to methods and kits for detecting an analyte in a test sample using acridinium-9-carboxylate aryl esters.

8 Claims, 17 Drawing Sheets

ACRIDINIUM PHENYL ESTERS USEFUL IN THE ANALYSIS OF BIOLOGICAL

RELATED APPLICATION INFORMATION

None.

FIELD OF THE INVENTION

The present invention relates to methods for detecting an analyte in a test sample. Specifically, the methods of the present invention employ certain acridinium-9-carboxylate aryl esters for detecting an analyte in a test sample. Additionally, the present invention also relates to kits for detecting an analyte in a test sample.

BACKGROUND OF THE INVENTION

Along with the progress in diagnostic or medical technology, various methods for detecting analytes of interest in test samples (such as serum, plasma, whole blood, etc.) have been developed and put into use to enable the early detection of various diseases and for confirming the effects of therapy. For the purpose of qualitative or quantitative detection of an analyte in a test sample, certain detectable compounds (also known as detectable labels or signal generating compounds) are used. Typically, these detectable compounds are capable of being used to generate detectable signals in the presence of one or more analytes in a test sample. In certain instances, these detectable compounds are attached to substances that have a certain affinity for the analyte to be detected and quantified. For example, an antibody can be conjugated to a detectable compound (the labeled antibody is referred to herein as a "conjugate"). The conjugate can then be used to detect and quantify the amount of an antigen of interest in a test sample. In other instances, however, the detectable compound is simply added to the test sample alone, not attached or conjugated to another substance (such as an antibody). Regardless of whether a detectable compound is attached or conjugated to another substance or used alone, once added to the test sample, the compound is activated and the signal detected. As a result, a determination of the presence of an analyte and the amount of the analyte contained in a test sample can be readily determined.

A variety of detectable compounds have been developed and used to generate detectable signals. Such compounds include, but are not limited to, radioactive substances, fluorescent substances, enzymes or metal colloids. In recent years, however, chemiluminescence methods using acridinium derivatives have drawn attention in view of their high sensitivity. Intense luminescence can be generated by reaction of acridinium derivatives with hydrogen peroxide under strong alkaline conditions (See, EP-A 830629 etc.). A number of acridinium derivatives are known in the art and are commercially available. While largely interchangeable, these acridinium derivatives can differ to at least some extent in terms of their physicochemical properties. Such differences can make a particular acridinium derivative either more or less preferred for the detection of an analyte of interest in a sample.

For this reason, there remains a need in the art for acridinium derivatives that can be employed for detecting an analyte in a test sample, as well as methods and kits for using such acridinium derivatives for the qualitative and/or quantitative detection of analyte. The present invention provides among other things such methods and kits.

SUMMARY OF THE INVENTION

In one embodiment, the present invention relates to a method of detecting an analyte of interest in a test sample. The method comprises the steps of:

a) processing a test sample to separate the analyte from protein in the test sample;

b) adding an acridinium-9-carboxylate aryl ester to the processed test sample, the acridinium-9-carboxylate aryl ester having a formula of:

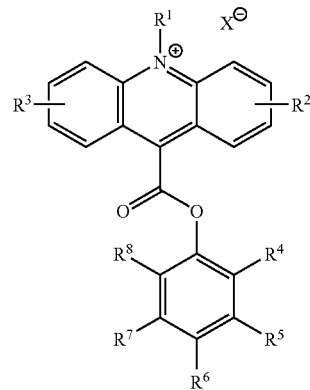

wherein $R^1$ is an alkyl, alkenyl, alkynyl, arylalkyl, aryl, sulfoalkyl or carboxyalkyl and $R^2$ through $R^8$ are each independently selected from the group consisting of: hydrogen, alkyl, amino, alkoxy, hydroxyl, carboxyl, halide, nitro, cyano, —$SO_3$, —NHC(O)R, —C(O)R, —C(O)OR, —C(O)NHR and —SCN, wherein R is an alkyl, alkenyl, alkynyl, arylalkyl, aryl, sulfoalkyl or carboxyalkyl; and X is an anion;

c) adding a basic solution to the processed test sample to generate a light signal; and d) quantifying the amount of analyte in the test sample by relating the amount of light generated in the test sample by comparison to a standard curve for the analyte.

In one aspect, the analyte of interest in the test sample comprises at least one peroxide. In another aspect, the method can further comprise the step of adding at least one analyte-specific enzyme which produces a peroxide to the test sample prior to step a) or after step a). The at least one analyte-specific enzyme which produces a peroxide can be selected from the group consisting of: dismutases, dehydrogenases, oxidases, reductases, synthases and combinations thereof. Exemplary analyte-specific enzymes which produce a peroxide are listed in Table 1.

The test sample used in the above method can be selected from the group consisting of: whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid and semen. Preferably, the analyte contained in the test sample is selected from the group consisting of: hydrogen peroxide, galactose, glucose, cholesterol, LDL, HDL, choline, lactic acid, uric acid, phosphatidylcholine, acetylcholine, phosphocholine, CDP-choline, lysophosphatidylcholine, triglycerides, phospholipase A2, phosholipase D, lysophosholipase D and sphingomyelin.

In the above method, the test sample is processed to separate or remove the analyte from protein that may be contained in the test sample. Any process known in the art to separate or remove protein from a test sample can be used. Specifically, a process that can be used to remove the protein can be selected from the group consisting of: ultrafiltration, extraction, precipitation, dialysis, chromatography and digestion.

The basic solution used in the above method is a solution that contains a base and that has a pH greater than or equal to 10, preferably, greater than or equal to 12.

In the above method, the standard curve used to quantify the amount of analyte in the test sample can be generated from solutions of the analyte of a known concentration.

In yet another embodiment, the present invention relates to a method of detecting an analyte in a test sample. The method comprises the steps of:

a) contacting the test sample containing the analyte with a specific binding partner to form an analyte specific binding partner complex;

b) separating the analyte specific binding partner complex from the test sample to form an analyte specific binding partner complex sample;

c) adding at least one analyte-specific enzyme which produces a peroxide to the analyte specific binding partner complex sample;

d) adding an acridinium-9-carboxylate aryl ester to the analyte specific binding partner complex sample, the acridinium-9-carboxylate aryl ester having a formula of:

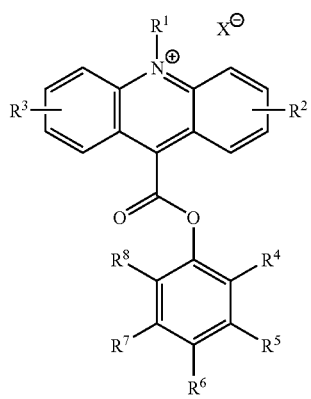

wherein $R^1$ is an alkyl, alkenyl, alkynyl, arylalkyl, aryl, sulfoalkyl or carboxyalkyl and $R^2$ through $R^8$ are each independently selected from the group consisting of: hydrogen, alkyl, amino, alkoxy, hydroxyl, carboxyl, halide, nitro, cyano, —$SO_3$, —NHC(O)R, —C(O)R, —C(O)OR, —C(O)NHR and —SCN, wherein R is an alkyl, alkenyl, alkynyl, arylalkyl, aryl, sulfoalkyl or carboxyalkyl; and X is an anion;

e) adding a basic solution to the analyte specific binding partner complex sample to generate a light signal; and f) quantifying the amount of analyte in the analyte specific binding partner complex sample by relating the amount of light generated in the test sample by comparison to a standard curve for the analyte.

The test sample used in the above method can be selected from the group consisting of: whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid and semen. Preferably, the analyte contained in the test sample is selected from the group consisting of: galactose, glucose, cholesterol, LDL, HDL, choline, lactic acid, uric acid, phosphatidylcholine, acetylcholine, phosphocholine, CDP-choline, lysophosphatidylcholine, triglycerides, phospholipase A2, phosholipase D, lysophosholipase D and sphingomyelin.

In the above method, the at one least analyte-specific enzyme which produces a peroxide is an enzyme listed in Table 1.

In the above method, the specific binding partner can be an antibody that binds to the analyte.

The basic solution used in the above method is a solution that contains a base and that has a pH greater than or equal to 10, preferably, greater than or equal to 12.

In the above method, the standard curve used to quantify the amount of analyte in the test sample can be generated from solutions of the analyte of a known concentration.

In yet another embodiment, the present invention relates to a method of detecting an analyte in a test sample. The method comprises the steps of:

a) contacting the test sample containing the analyte with a specific binding partner having conjugated thereon at least one substrate-specific enzyme which produces a peroxide, to form an analyte:specific binding partner conjugate complex;

b) separating the analyte-specific binding partner conjugate complex from the test sample to form an analyte-specific binding partner conjugate complex sample;

c) adding at least one substrate to the analyte-specific binding partner conjugate complex sample;

d) adding an acridinium-9-carboxylate aryl ester to the analyte-specific binding partner conjugate complex sample, the acridinium-9-carboxylate aryl ester having a formula of:

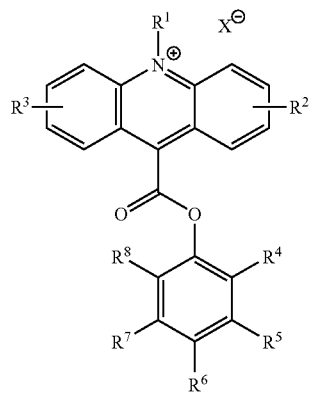

wherein $R^1$ is an alkyl, alkenyl, alkynyl, arylalkyl, aryl, sulfoalkyl or carboxyalkyl and $R^2$ through $R^8$ are each independently selected from the group consisting of: hydrogen, alkyl, amino, alkoxy, hydroxyl, carboxyl, halide, nitro, cyano, —$SO_3$, —NHC(O)R, —C(O)R, —C(O)OR, —C(O)NHR and —SCN, wherein R is an alkyl, alkenyl, alkynyl, arylalkyl, aryl, sulfoalkyl or carboxyalkyl; and X is an anion;

e) adding a basic solution to the analyte-specific binding partner conjugate complex sample to generate a light signal; and f) quantifying the amount of analyte in the test sample by relating the amount of light generated in the analyte-specific binding partner conjugate complex sample by comparison to a standard curve for the analyte.

The test sample used in the above method can be selected from the group consisting of: whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid and semen.

In the above method, the at least one substrate-specific enzyme which produces a peroxide is one of the enzymes listed in Table 1. In the above method, the at least one substrate is one of the substrates listed in Table 1. In the above method, the specific binding partner can be an antibody that binds to the analyte.

The basic solution used in the above method is a solution that contains a base and that has a pH greater than or equal to 10, preferably, greater than or equal to 12.

In the above method, the standard curve used to quantify the amount of analyte in the test sample can be generated from solutions of the analyte of a known concentration.

In another embodiment, the present invention relates to a kit for use in detecting an analyte in a test sample. The kit can comprise the following:

a. acridinium-9-carboxylate aryl ester having a formula of:

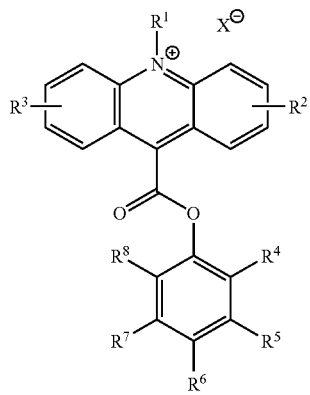

wherein $R^1$ is an alkyl, alkenyl, alkynyl, arylalkyl, aryl, sulfoalkyl or carboxyalkyl and $R^2$ through $R^8$ are each independently selected from the group consisting of: hydrogen, alkyl, amino, alkoxy, hydroxyl, carboxyl, halide, nitro, cyano, —$SO_3$, —NHC(O)R, —C(O)R, —C(O)OR, —C(O)NHR and —SCN, wherein R is an alkyl, alkenyl, alkynyl, arylalkyl, aryl, sulfoalkyl or carboxyalkyl; and X is an anion;

b. at least one basic solution; and
c. instructions for detecting an analyte in a test sample.

At least one of the instructions contained in the test kit describe processing a test sample to separate the analyte from protein contained in the test sample.

Optionally, the kit can further comprise at least one analyte-specific enzyme which produces a peroxide.

In another embodiment, the present invention relates to a kit for use in detecting an analyte in a test sample. The kit can comprise the following:

a. acridinium-9-carboxylate aryl ester having a formula of:

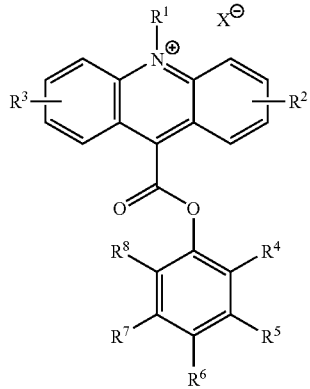

wherein $R^1$ is an alkyl, alkenyl, alkynyl, arylalkyl, aryl, sulfoalkyl or carboxyalkyl and $R^2$ through $R^8$ are each independently selected from the group consisting of: hydrogen, alkyl, amino, alkoxy, hydroxyl, carboxyl, halide, nitro, cyano, —$SO_3$, —NHC(O)R, —C(O)R, —C(O)OR, —C(O)NHR and —SCN, wherein R is an alkyl, alkenyl, alkynyl, arylalkyl, aryl, sulfoalkyl or carboxyalkyl; and X is an anion;

b. at least one specific binding partner;
c. at least one basic solution; and
d. instructions for detecting an analyte in a test sample.

The at least one specific binding partner contained in the kit can be at least one antibody that binds to the analyte.

The kit can further comprise at least one analyte-specific enzyme which produces a peroxide.

The specific binding partner contained in the kit can also have conjugated thereon at least one substrate-specific enzyme which produces a peroxide. The at least one substrate-specific enzyme can be an enzyme listed in Table 1. If the specific binding partner has conjugated thereon at least one substrate-specific enzyme which produces a peroxide, then the kit can further comprise at least one substrate. The substrate can be a substrate listed in Table 1.

DETAILED DESCRIPTION OF THE INVENTION

Figure 1:
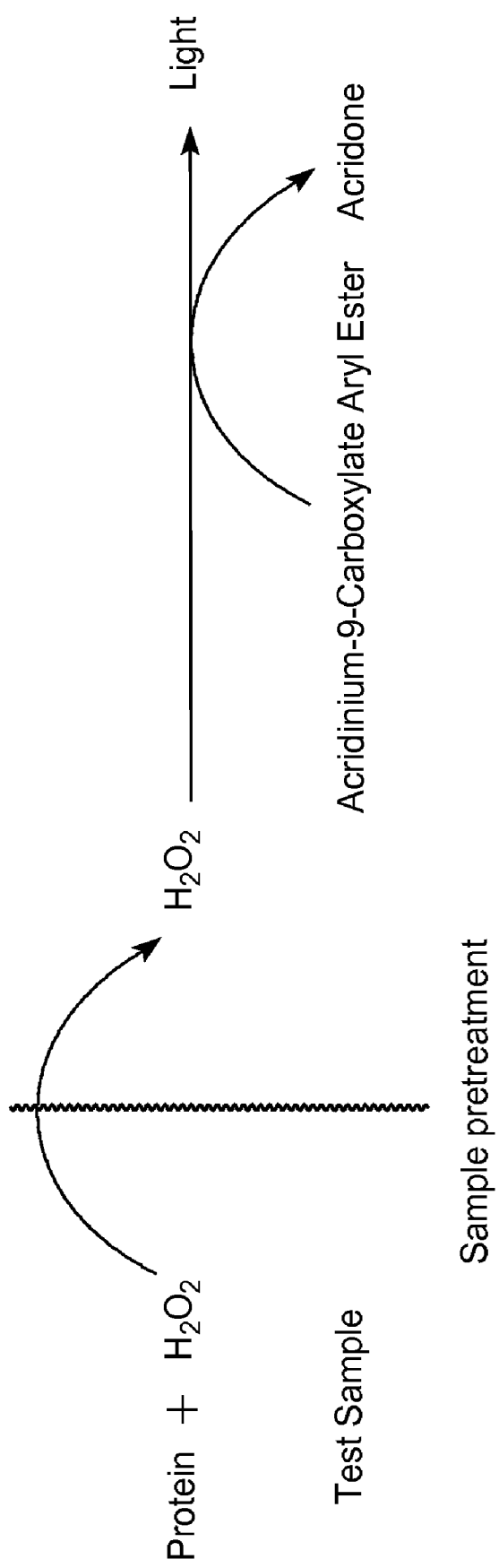
FIG. 1 is a non-limiting illustration of one aspect of the method of the present invention, wherein the analyte of interest in the test sample is a peroxide, specifically, hydrogen peroxide. The test sample is pretreated prior to the addition of the acridinium-9-carboxylate aryl ester.

The present invention provides among other things methods and kits for using acridinium derivatives for the qualitative and/or quantitative detection of analyte. Unexpectedly and surprisingly, the inventors of the present invention found that acridinium-9-carboxylate aryl esters are extremely sensitive to protein contained in test samples. Specifically, the inventors found that acridinium-9-carboxylate aryl esters lose their intense chemiluminescent properties in the presence of protein in a test sample, thus rendering these esters virtually unusable for use in identifying the presence of an analyte in a test sample. In view thereof, methods for restoring the intense chemiluminescent properties of the acridinium-9-carboxylate esters make these acridinium-9-carboxylate aryl esters useful for use in identifying the presence of an analyte in a test sample. This is described in more detail below.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Definitions As used herein, the term "alkenyl" means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

As used herein, the term "alkylcarbonyl," means an alkyl group attached to the parent molecular moiety through a carbonyl group.

As used herein, the term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkynyl" means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

As used herein, the term "amino" means —$NR_aR_b$, wherein $R_a$ and $R_b$ are independently selected from the group consisting of hydrogen, alkyl and alkylcarbonyl.

As used herein, the term "analyte" or "analyte of interest" as used interchangeably herein, generally refers to a substance to be detected. Analytes may include inorganic substances, including, but not limited to, hydrogen peroxide and sulfite. Analytes may include antigenic substances, haptens, antibodies, and combinations thereof. Analytes include, but are not limited to, toxins, organic compounds, DNA, RNA, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include, but are not limited to, brain natriuretic peptide (BNP) 1-32; NT-proBNP; proBNP; preproBNP; troponin I; troponin T; troponin C; human neutrophil gelatinase-associated lipocalin (hNGAL); tacrolimus; sirolimus; cyclosporine; ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 micro-globulin; glycated hemoglobin (Gly. Hb); cortisol; digitoxin; N-acetyl-procainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HbsAg); antibodies to hepatitis B core antigen, such as anti-hepatitis B core antigen IgG and IgM (Anti-HBC); human immune deficiency virus (HIV); human T-cell leukemia virus (HTLV); hepatitis B e antigen (HbeAg); antibodies to hepatitis B e antigen (Anti-Hbe); influenza virus; thyroid stimulating hormone (TSH); thyroxine (T4); total triiodothyronine (Total T3); free triiodothyronine (Free T3); carcinoembryonic antigen (CEA); lipoproteins, cholesterol, and triglycerides; galactose, glucose, LDL, HDL, choline, lactic acid, uric acid, phosphatidylcholine, acetylcholine, phosphocholine, CDP-choline, lysophosphatidylcholine, phospholipase A2, phosholipase D, lysophosholipase D and sphingomyelin and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as propoxy and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyphene.

As used herein, the phrases "analyte-specific enzyme" or "substrate-specific enzyme" refer to enzymes which produce a peroxide, including, dismutases, dehydrogenases, oxidases, reductases, synthases or combinations thereof Exemplary analyte-specific enzymes which produce a peroxide are listed below in Table 1. Many analyte-specific enzymes/substrate-specific enzymes that produce a peroxide are known in the art. For example, analyte-specific enzymes/substrate-specific enzymes which produces a peroxide can be conveniently found in on the on the World Wide Web at the Enzyme Nomenclature Database and the Enzyme Database (developed at Trinity College in Dublin, Ireland).

TABLE 1

| ACCEPTED COMMON NAME | IUBMB ENZYME NOMENCLATURE | PREFERRED SUBSTRATE |
| --- | --- | --- |
| (R)-6-hydroxynicotine oxidase | EC 1.5.3.6 | (R)-6-hydroxynicotine |
| (S)-2-hydroxy acid oxidase | EC 1.1.3.15 | S)-2-hydroxy acid |
| (S)-6-hydroxynicotine oxidase | EC 1.5.3.5 | (S)-6-hydroxynicotine |
| 3-aci-nitropropanoate oxidase | EC 1.7.3.5 | 3-aci-nitropropanoate |
| 3-hydroxyanthranilate oxidase | EC 1.10.3.5 | 3-hydroxyanthranilate |
| 4-hydroxymandelate oxidase | EC 1.1.3.19 | (S)-2-hydroxy-2-(4-hydroxyphenyl)acetate |
| 6-hydroxynicotinate dehydrogenase | EC 1.17.3.3 | 6-hydroxynicotinate |
| Abscisic-aldehyde oxidase | EC 1.2.3.14 | abscisic aldehyde |
| acyl-CoA oxidase | EC 1.3.3.6 | acyl-CoA |
| Alcohol oxidase | EC 1.1.3.13 | a primary alcohol |
| aldehyde oxidase | EC 1.2.3.1 | an aldehyde |
| amine oxidase | | |

TABLE 1-continued

| ACCEPTED COMMON NAME | IUBMB ENZYME NOMENCLATURE | PREFERRED SUBSTRATE |
|---|---|---|
| amine oxidase (copper-containing) | EC 1.4.3.6 | primary monoamines, diamines and histamine |
| amine oxidase (flavin-containing) | EC 1.4.3.4 | a primary amine |
| aryl-alcohol oxidase | EC 1.1.3.7 | an aromatic primary alcohol (2-naphthyl)methanol 3-methoxybenzyl alcohol |
| aryl-aldehyde oxidase | EC 1.2.3.9 | an aromatic aldehyde |
| catechol oxidase | EC 1.1.3.14 | catechol |
| cholesterol oxidase | EC 1.1.3.6 | cholesterol |
| choline oxidase | EC 1.1.3.17 | choline |
| columbamine oxidase | EC 1.21.3.2 | columbamine |
| cyclohexylamine oxidase | EC 1.4.3.12 | cyclohexylamine |
| cytochrome c oxidase | EC 1.9.3.1 | |
| D-amino-acid oxidase | EC 1.4.3.3 | a D-amino acid |
| D-arabinono-1,4-lactone oxidase | EC 1.1.3.37 | D-arabinono-1,4-lactone |
| D-arabinono-1,4-lactone oxidase | EC 1.1.3.37 | D-arabinono-1,4-lactone |
| D-aspartate oxidase | EC 1.4.3.1 | D-aspartate |
| D-glutamate oxidase | EC 1.4.3.7 | D-glutamate |
| D-glutamate(D-aspartate) oxidase | EC 1.4.3.15 | D-glutamate |
| dihydrobenzophenanthridine oxidase | EC 1.5.3.12 | dihydrosanguinarine |
| dihydroorotate oxidase | EC 1.3.3.1 | (S)-dihydroorotate |
| dihydrouracil oxidase | EC 1.3.3.7 | 5,6-dihydrouracil |
| dimethylglycine oxidase | EC 1.5.3.10 | N,N-dimethylglycine |
| D-mannitol oxidase | EC 1.1.3.40 | mannitol |
| ecdysone oxidase | EC 1.1.3.16 | ecdysone |
| ethanolamine oxidase | EC 1.4.3.8 | ethanolamine |
| galactose oxidase | EC 1.1.3.9 | D-galactose |
| glucose oxidase | EC 1.1.3.4 | β-D-glucose |
| glutathione oxidase | EC 1.8.3.3 | glutathione |
| glycerol-3-phosphate oxidase | EC 1.1.3.21 | sn-glycerol 3-phosphate |
| glycine oxidase | EC 1.4.3.19 | glycine |
| glyoxylate oxidase | EC 1.2.3.5 | glyoxylate |
| hexose oxidase | EC 1.1.3.5 | D-glucose, D-galactose D-mannose maltose lactose cellobiose |
| hydroxyphytanate oxidase | EC 1.1.3.27 | L-2-hydroxyphytanate |
| indole-3-acetaldehyde oxidase | EC 1.2.3.7 | (indol-3-yl)acetaldehyde |
| lactic acid oxidase | | Lactic acid |
| L-amino-acid oxidase | EC 1.4.3.2 | an L-amino acid |
| L-aspartate oxidase | EC 1.4.3.16 | L-aspartate |
| L-galactonolactone oxidase | EC 1.3.3.12 | L-galactono-1,4-lactone |
| L-glutamate oxidase | EC 1.4.3.11 | L-glutamate |
| L-gulonolactone oxidase | EC 1.1.3.8 | L-gulono-1,4-lactone |
| L-lysine 6-oxidase | EC 1.4.3.20 | L-lysine |
| L-lysine oxidase | EC 1.4.3.14 | L-lysine |
| long-chain-alcohol oxidase | EC 1.1.3.20 | A long-chain-alcohol |
| L-pipecolate oxidase | EC 1.5.3.7 | L-pipecolate |
| L-sorbose oxidase | EC 1.1.3.11 | L-sorbose |
| malate oxidase | EC 1.1.3.3 | (S)-malate |
| methanethiol oxidase | EC 1.8.3.4 | methanethiol |
| monoamino acid oxidase | | |
| $N^6$-methyl-lysine oxidase | EC 1.5.3.4 | 6-N-methyl-L-lysine |
| N-acylhexosamine oxidase | EC 1.1.3.29 | N-acetyl-D-glucosamine N-glycolylglucosamine N-acetylgalactosamine N-acetylmannosamine. |
| NAD(P)H oxidase | EC 1.6.3.1 | NAD(P)H |
| nitroalkane oxidase | EC 1.7.3.1 | a nitroalkane |
| N-methyl-L-amino-acid oxidase | EC 1.5.3.2 | an N-methyl-L-amino acid |
| nucleoside oxidase | EC 1.1.3.39 | adenosine |
| oxalate oxidase | EC 1.2.3.4 | oxalate |
| polyamine oxidase | EC 1.5.3.11 | 1-N-acetylspermine |
| polyphenol oxidase | EC 1.14.18.1 | |
| polyvinyl-alcohol oxidase | EC 1.1.3.30 | polyvinyl alcohol |
| prenylcysteine oxidase | EC 1.8.3.5 | an S-prenyl-L-cysteine |
| protein-lysine 6-oxidase | EC 1.4.3.13 | peptidyl-L-lysyl-peptide |
| putrescine oxidase | EC 1.4.3.10 | butane-1,4-diamine |
| pyranose oxidase | EC 1.1.3.10 | D-glucose D-xylose L-sorbose D-glucono-1,5-lactone |

TABLE 1-continued

| ACCEPTED COMMON NAME | IUBMB ENZYME NOMENCLATURE | PREFERRED SUBSTRATE |
|---|---|---|
| pyridoxal 5'-phosphate synthase | EC 1.4.3.5 | pyridoxamine 5'-phosphate |
| pyridoxine 4-oxidase | EC 1.1.3.12 | pyridoxine |
| pyrroloquinoline-quinone synthase | EC 1.3.3.11 | 6-(2-amino-2-carboxyethyl)-7,8-dioxo-1,2,3,4,5,6,7,8-octahydroquinoline-2,4-dicarboxylate |
| pyruvate oxidase | EC 1.2.3.3 | pyruvate |
| pyruvate oxidase (CoA-acetylating) | EC 1.2.3.6 | pyruvate |
| reticuline oxidase | EC 1.21.3.3 | reticuline |
| retinal oxidase | EC 1.2.3.11 | retinal |
| rifamycin-B oxidase | EC 1.10.3.6 | rifamycin-B |
| sarcosine oxidase | EC 1.5.3.1 | sarcosine |
| secondary-alcohol oxidase | EC 1.1.3.18 | a secondary alcohol |
| sulfite oxidase | EC 1.8.3.1 | sulfite |
| superoxide dismutase | EC 1.15.1.1 | superoxide |
| superoxide reductase | EC 1.15.1.2 | superoxide |
| tetrahydroberberine oxidase | EC 1.3.3.8 | (S)-tetrahydroberberine |
| thiamine oxidase | EC 1.1.3.23 | thiamine |
| tryptophan α,β-oxidase | EC 1.3.3.10 | L-tryptophan |
| urate oxidase (uricase, uric acid oxidase) | EC 1.7.3.3 | uric acid |
| vanillyl-alcohol oxidase | EC 1.1.3.38 | vanillyl alcohol |
| xanthine oxidase | EC 1.17.3.2 | xanthine |
| xylitol oxidase | EC 1.1.3.41 | xylitol |

As used herein, the term "anion" refers to an anion of an inorganic or organic acid, such as, but not limited to, hydrochloric acid, hydrobromic acid, sulfuric acid, methane sulfonic acid, formic acid, acetic acid, oxalic acid, succinic acid, tartaric acid, mandelic acid, fumaric acid, lactic acid, citric acid, glutamic acid, aspartic acid, phosphate, trifluoromethansulfonic acid, trifluoroacetic acid and fluorosulfonic acid and any combinations thereof.

As used herein, the term "aryalkyl" means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

As used herein, the term "aryl" means a phenyl group, or a bicyclic or tricyclic fused ring system wherein one or more of the fused rings is a phenyl group. Bicyclic fused ring systems are exemplified by a phenyl group fused to a cycloalkenyl group, as defined herein, a cycloalkyl group, as defined herein, or another phenyl group. Tricyclic fused ring systems are exemplified by a bicyclic fused ring system fused to a cycloalkenyl group, as defined herein, a cycloalkyl group, as defined herein or another phenyl group. Representative examples of aryl include, but are not limited to, anthracenyl, azulenyl, fluorenyl, indanyl, indenyl, naphthyl, phenyl, and tetrahydronaphthyl. The aryl groups of the present invention can be optionally substituted with one-, two, three, four, or five substituents independently selected from the group consisting of alkoxy, alkyl, carboxyl, halo, and hydroxyl.

As used herein, the term "carbonyl" refers to —C(O)—.

As used herein, the term "carboxy" or "carboxyl" refers to —CO$_2$H.

As used herein, the term "carboxyalkyl" refers to an alkyl group that is substituted with one or more carboxy groups.

As used herein, the term "cyano" means a —CN group.

As used herein, the term "cycloalkenyl," refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine-to ten-membered ring has one to four double bonds. Examples of cycloalkenyl groups include cyclohexenyl, octahydronaphthalenyl, norbornylenyl, and the like. The cycloalkenyl groups of the present invention can be optionally substituted with one, two, three, four, or five substituents independently selected from the group consisting of alkoxy, alkyl, carboxyl, halo, and hydroxyl.

As used herein, the term "cycloalkyl" refers to a saturated monocyclic, bicyclic, or tricyclic hydrocarbon ring system having three to twelve carbon atoms. Examples of cycloalkyl groups include cyclopropyl, cyclopentyl, bicyclo[3.1.1]heptyl, adamantyl, and the like. The cycloalkyl groups of the present invention can be optionally substituted with one, two, three, four, or five substituents independently selected from the group consisting of alkoxy, alkyl, carboxyl, halo, and hydroxyl.

As used herein, the term "halide" means a —Cl, —Br, —I or —F.

As used herein, the term "hydroxyl" means an —OH group.

As used herein, the term "nitro" means a —NO$_2$ group.

As used herein, the term "sulfoalkyl" refers to an alkyl group to which a sulfonate group is bonded, wherein the alkyl is bonded to the molecule of interest.

As used herein, the phrase "specific binding partner," as used herein, is a member of a specific binding pair. That is, two different molecules where one of the molecules, through chemical or physical means, specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors, and enzymes and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal and complexes thereof, including those formed by recombinant DNA molecules.

As used herein, the term "test sample" generally refers to a biological material being tested for and/or suspected of containing an analyte of interest. The test sample may be derived from any biological source, such as, a physiological fluid, including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen and so forth. Besides physiological fluids, other liquid samples may be used such as water, food products, and so forth, for the performance of environmental or food production assays. In addition, a solid material suspected of containing the analyte may be used as the test sample. The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

Assay for Detecting an Analyte of Interest

In general, the present invention relates to an assay for detecting an analyte of interest in a test sample. Specifically, as will be described in more detail below, in the assay of the present invention, the processing of the test sample containing the analyte of interest to separate or remove protein contained in the test sample or the removal or separation of the analyte of interest from the test sample (and thus away from protein contained in the test sample) allows for the use of one or more acridinium esters having a particular formula in the quantification of the amount of analyte contained in the test sample. In fact, until the discovery of the present invention, the one or more acridinium esters having the formula described herein typically were not used in the quantification of the amount of analyte in the test sample due to sensitivity of these acridinium esters in the presence of protein.

The assay or method of the present invention involves obtaining a test sample from a subject. A subject from which a test sample can be obtained is any vertebrate. Preferably, the vertebrate is a mammal. Examples of mammals include, but are not limited to, dogs, cats, rabbits, mice, rats, goats, sheep, cows, pigs, horses, non-human primates and humans. The test sample can be obtained from the subject using routine techniques known to those skilled in the art. Preferably, the test sample naturally contains peroxide or contains a compound, protein or peptide for which there exists one or more analyte-specific enzymes that can be used to generate peroxide, such as, at least one dismutase, dehydrogenase, oxidase, reductase or synthase or a combination of at least one dismutase, dehydrogenase, oxidase, reductase or synthase. For example, if the analyte of interest is hydrogen peroxide, no analyte-specific enzyme is necessary. However, if the analyte of interest is choline, then the analyte-specific enzyme could be choline oxidase. Alternatively, if the analyte of interest is lactate, then the analyte-specific enzyme could be lactic acid oxidase.

In one embodiment, the test sample containing the analyte of interest comprises a peroxide, such as hydrogen peroxide (See, FIG. 1). The peroxide containing test sample (containing the analyte of interest) is manipulated or processed in such a manner so as to separate or remove protein that may be contained in the test sample (thus resulting in a processed test sample). Methods for separating or removing proteins from test samples are well known to those skilled in the art and include, but are not limited to, ultrafiltration, extraction, precipitation, dialysis, chromatography and digestion. Techniques for separating or removing proteins using ultrafiltration, extraction, precipitation, dialysis and chromatography are well known to those skilled in the art (See, for example, Wells, D. (2003) *High Throughput Bioanalytical Sample Preparation. Methods and Automation Strategies*, Elsevier.). The amount of protein removed or separated from the test sample can be about 40%, about 45%, about 50%, about 55%, about 60%, about 65%, about 70%, about 75%, about 80%, about 85%, about 90% and about 95%.

After the separation of protein from the test sample, then the peroxide contained in the processed test sample can be converted to an end product having a distinct chemiluminescent emission. Such an end product is produced by adding to the processed test sample at least one acridinium ester. Preferably, the acridinium ester is an acridinium-9-carboxylate aryl ester has the formula of formula I shown below:

wherein $R^1$ is an alkyl, alkenyl, alkynyl, arylalkyl, aryl, sulfoalkyl or carboxyalkyl and $R^2$ through $R^8$ are each independently selected from the group consisting of: hydrogen, alkyl, amino, alkoxy, hydroxyl, carboxyl, halide, nitro, cyano, $-SO_3$, $-NHC(O)R$, $-C(O)R$, $-C(O)OR$, $-C(O)NHR$ and $-SCN$, wherein R is an alkyl, alkenyl, alkynyl, arylalkyl, aryl, sulfoalkyl or carboxyalkyl; and X is an anion. Examples of acridinium-9-carboxylate aryl esters having the above formula that can be used in the present invention include, but are not limited to, 10-methyl-9-(phenoxycarbonyl)acridinium fluorosulfonate (available from Cayman Chemical, Ann Arbor, Mich.). Methods for preparing acridinium 9-carboxylate aryl esters are described in McCapra, F., et al., *Photochem. Photobiol.*, 4, 1111-21 (1965); Razavi, Z et al., *Luminescence*, 15:245-249 (2000); Razavi, Z et al., *Luminescence*, 15:239-244 (2000); and U.S. Pat. No. 5,241,070.

Figure 13:
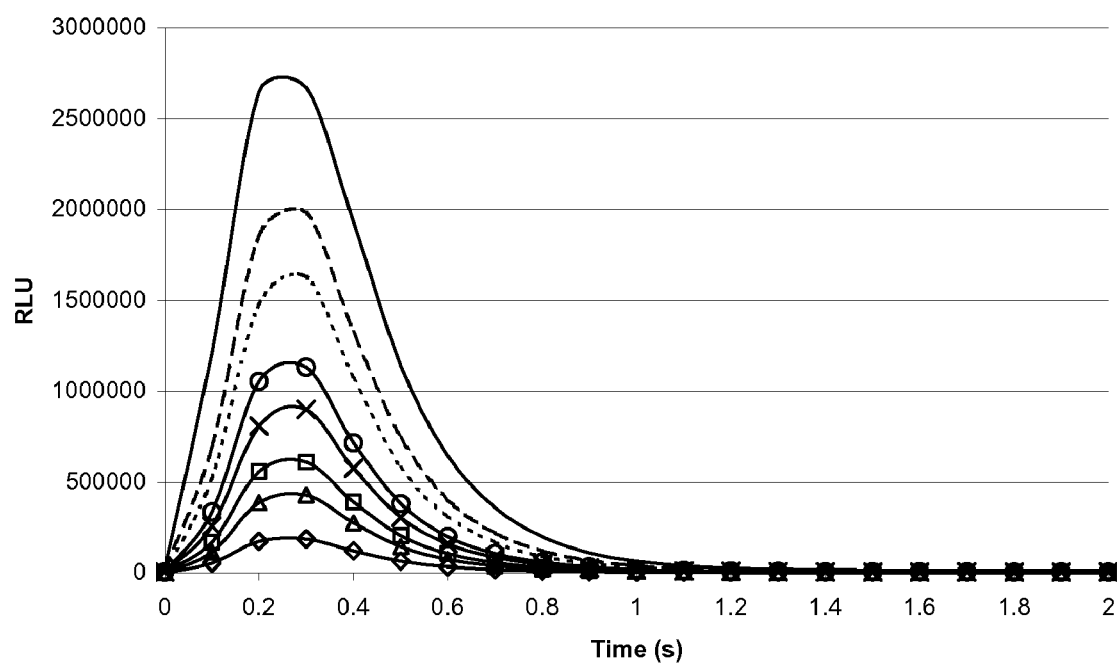
FIG. 13 shows chemiluminescence profiles for 2 µM of 10-methyl-9-(phenoxycarbonyl)acridinium fluorosulfonate at pH 4. Abscissa: time in seconds ("Time(s)"). Ordinate: relative light units ("RLU"). Symbols: solid line, 150 µM choline; dashed line, 75 µM choline; dotted line, 50 µM choline; -○-, 30 µM choline; -x-, 20 µM choline; -□-, 10 µM choline; -Δ-, 5 µM choline; -◇-, 0 µM choline.

Acridinium-9-carboxylate aryl esters having the above formula I are readily (commercially) available. Additionally, it is surprising that the acridinium-9-carboxylate aryl esters having the above formula are more efficient chemiluminescent indicators for hydrogen peroxide produced in the oxidation of the analyte by at least one oxidase, at least one both in the intensity of the signal and in the rapidity of the signal. By comparison of the acridinium-9-carboxylate aryl ester, 10-methyl-9-(phenoxycarbonyl)acridinium fluorosulfonate (FIG. 13). Chemiluminescence profiles for 2 μM of 10-methyl-9-(phenoxycarbonyl)acridinium fluorosulfonate at pH 4) and the acridinium-9-carboxamide, 9-[[(3-carboxypropyl)

Figure 21:
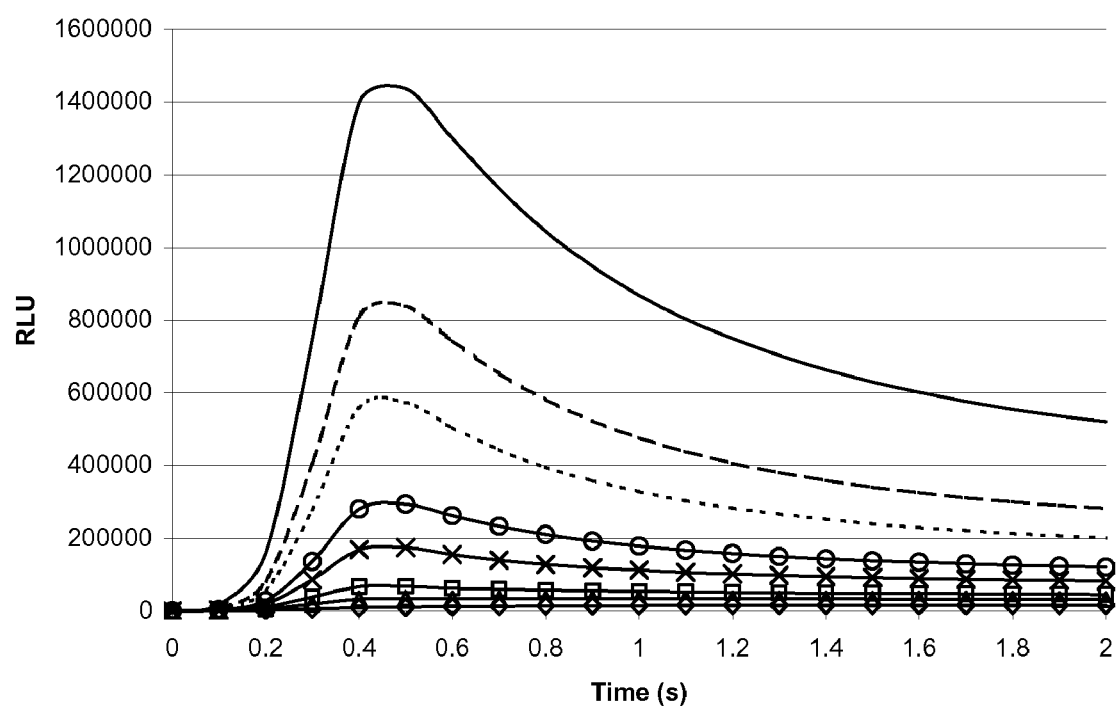
FIG. 21 shows chemiluminescence profiles for 4 µM 9-[[(3-carboxypropyl)[(4-methylphenyl)sulfonyl]amino]-carbonyl]-10-(3-sulfopropyl)acridinium inner salt. Abscissa: time in seconds ("Time(s)"). Ordinate: relative light units ("RLU"). Symbols: solid line, 150 µM choline; dashed line, 75 µM choline; dotted line, 50 µM choline; -○-, 30 µM choline; -x-, 20 µM choline; -□-, 10 µM choline; -Δ-, 5 µM choline; -◇-, 0 µM choline.
Figure 22:
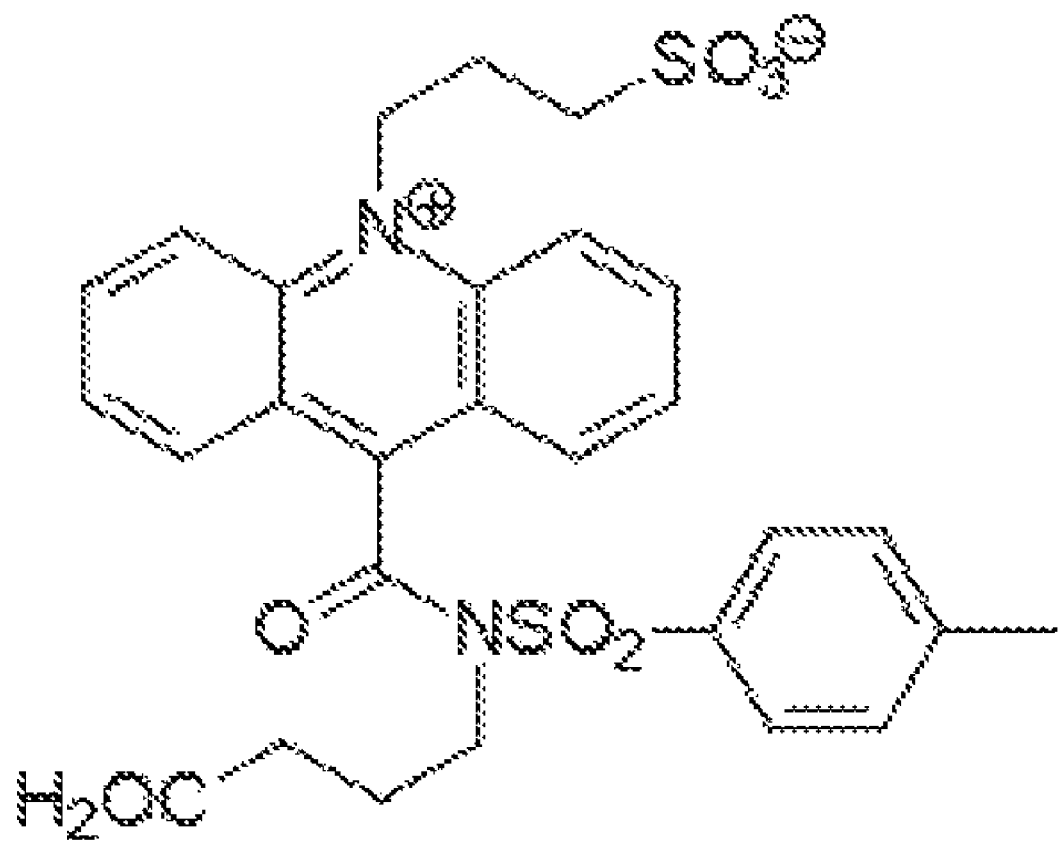
FIG. 22 shows the structure of 9-[[(3-carboxypropyl)[(4-methylphenyl)sulfonyl]amino]-carbonyl]-10-(3-sulfopropyl)acridinium inner salt.

[(4-methylphenyl)sulfonyl]amino]-carbonyl]-10-(3-sulfopropyl)acridinium inner salt (FIG. 21). Chemiluminescence profiles for 4 μM 9-[[(3-carboxypropyl)[(4-methylphenyl)sulfonyl]amino]-carbonyl]-10-(3-sulfopropyl)acridinium inner salt), the former reaches a peak light intensity that is double that of the latter. Further, that increased efficiency is achieved at half the molar concentration. Still further, the course of the chemiluminescent emission for the acridinium-9-carboxylate aryl ester is completed rapidly, in under 1 second, while the acridinium-9-carboxamide chemiluminescent emission extends over 2 seconds.

After the addition of the acridinium-9-carboxylate aryl ester to the processed test sample, at least one basic solution is added to the test sample in order to generate a detectable signal, namely, a chemiluminescent signal. The basic solution is a solution that contains at least one base and that has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate. The amount of basic solution added to the processed test sample depends on the concentration of the basic solution used in the method. Based on the concentration of the basic solution used, one skilled in the art could easily determine the amount of basic solution to be used in the method.

The chemiluminescent signal that is generated can then be detected using routine techniques known to those skilled in the art. Thus, in the assay of the present invention, the chemiluminescent signal generated after the addition of a basic solution, indicates the presence of the analyte of interest. The amount of the analyte in the test sample can be quantified based on the intensity of the signal generated. Specifically, the amount of analyte contained in a test sample is either proportional or inversely proportional to the intensity of the signal generated. For example, in some instances, a high signal intensity may be generated by the lowest concentration of analyte in the test sample (in this instance, the amount of analyte in the test sample is inversely proportional to the amount of signal generated). Specifically, the amount of the analyte of interest present can be quantified based on comparing the amount of light generated to a standard curve for the analyte or by comparison to a reference standard. The standard curve can be generated using serial dilutions or solutions of analyte of interest of known concentration, by mass spectroscopy, gravimetrically and by other techniques known in the art.

In a second embodiment, the test sample containing an analyte of interest does not contain or comprise a peroxide. However, it is preferred that for the analyte of interest to be detected that there exist one or more analyte-specific enzymes that can be added to the test sample in order to generate peroxide in the test sample. Preferably, the analyte of interest is galactose, glucose, cholesterol, LDL, HDL, choline, lactic acid, uric acid, phosphatidylcholine, acetylcholine, phosphocholine, CDP-choline, lysophosphatidylcholine, triglycerides, phospholipase A2, phosholipase D, lysophosholipase D and sphingomyelin. The test sample is manipulated or processed in such a manner so as to separate or remove from the test sample protein that may be contained in the test sample (thus forming a processed test sample). The methods for separating or removing proteins in the test sample are the separation methods described above, such as, but not limited to, ultrafiltration, extraction, precipitation, dialysis, chromatography and digestion.

Either before or after the separation of protein from the test sample, at least one analyte-specific enzyme, such as, at least one dismutase, dehydrogenase, oxidase, reductase or synthase or a combination of at least one dismutase, dehydrogenase, oxidase, reductase or synthase, is added to the test sample. Examples of at least one analyte-specific enzyme that can be used are selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, arylaldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, $N^6$-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof Preferably, the amount of at least one analyte-specific enzyme that can be added to the test sample is from about 0.0001 unit/mL to about 10,000 units/mL.

Figure 2:
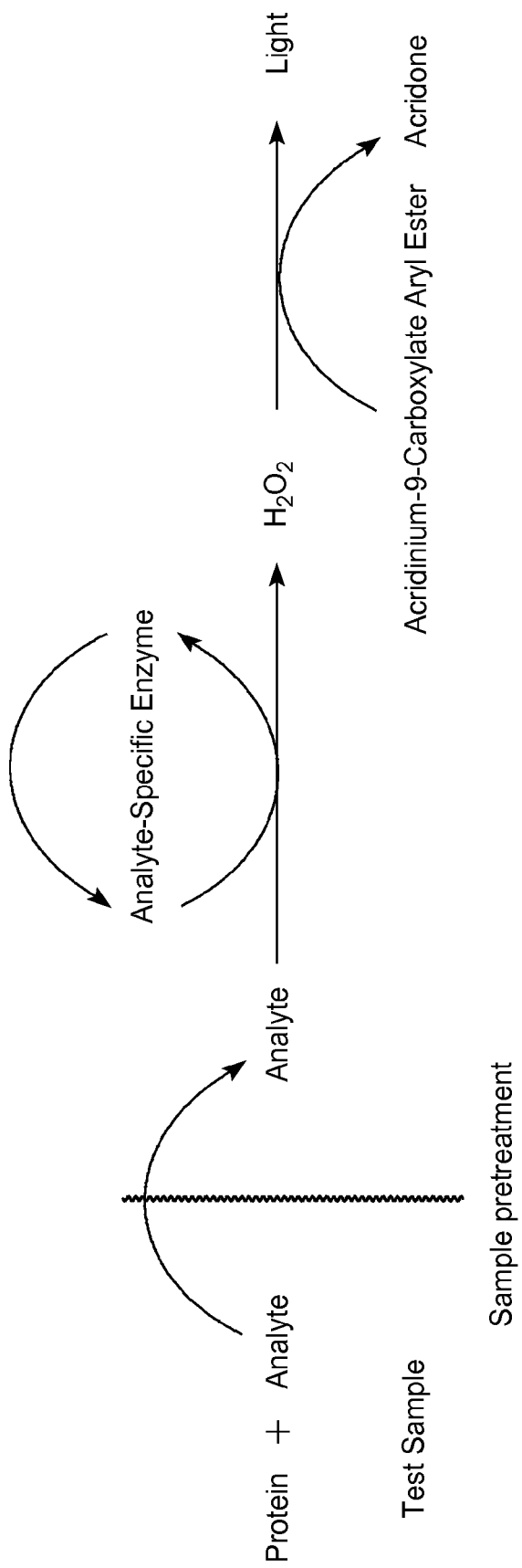
FIG. 2 is a non-limiting illustration of another aspect of the method of the present invention, wherein at least one analyte-specific enzyme which produces a peroxide is added to the test sample containing the analyte of interest. In this aspect, the at least one analyte-specific enzyme which produces a peroxide, is added to generate peroxide, specifically, hydrogen peroxide. The test sample is pretreated to separate the analyte of interest from protein in the test sample prior to the addition of the analyte-specific enzyme which produces a peroxide and the acridinium-9-carboxylate aryl ester.
Figure 3:
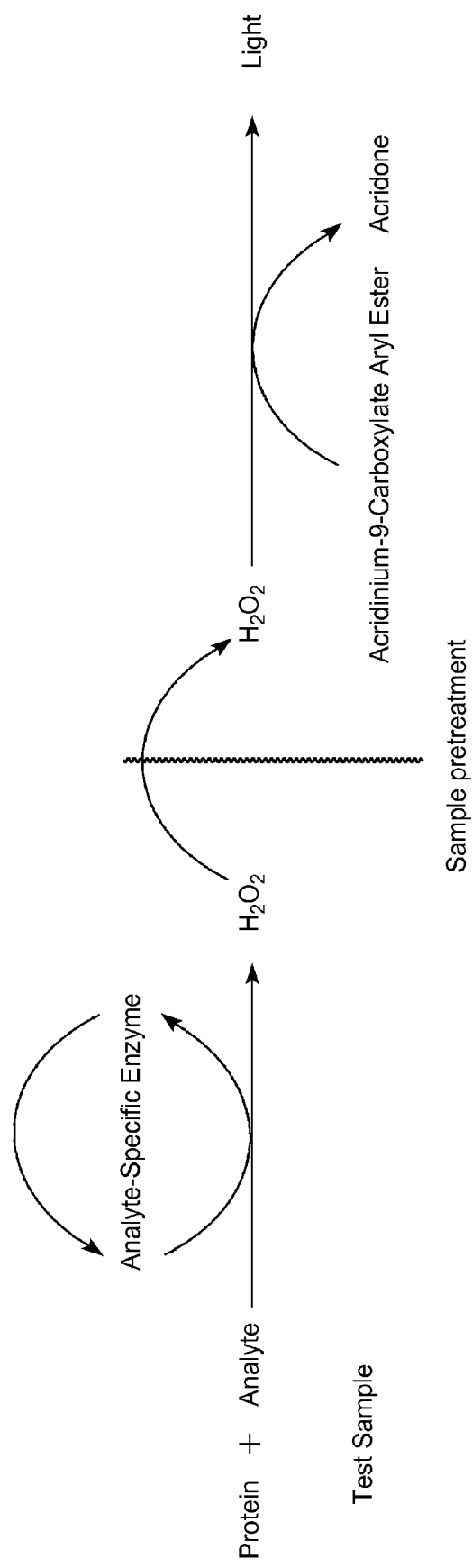
FIG. 3 is a non-limiting illustration of another aspect of the method of the present invention wherein at least one analyte-specific enzyme which produces a peroxide, is added to the test sample containing the analyte of interest. In this aspect, the at least one analyte-specific enzyme which produces a peroxide, is added to generate peroxide, specifically, hydrogen peroxide. The test sample is pretreated to separate the hydrogen peroxide from protein in the test sample prior to the addition of the acridinium-9-carboxylate aryl ester.

As alluded to above, the time at which the at least one analyte-specific enzyme is added to the test sample is not critical, provided that it is added before the addition of the at least one acridinium ester having the formula of formula I, which was previously discussed herein. Thus, for example, the at least one analyte-specific enzyme is added to the test sample after the test sample has been processed to separate or remove the protein (See, FIG. 2). Alternatively, in another aspect, the at least one analyte-specific enzyme is added to the test sample before the test sample is processed to separate or remove the protein from the test sample (See, FIG. 3).

Preferably, the at least one analyte-specific enzyme is at least one oxidase. Oxidases can be used to generate hydrogen peroxide in a test sample. The peroxide that is generated by the addition of the at least analyte-specific enzyme can then be converted to an end product having a distinct chemiluminescent emission. Such an end product is produced by adding to the processed test sample at least one acridinium ester.

Preferably, the acridinium ester is an acridinium-9-carboxylate aryl ester having a formula of formula I, which was discussed previously herein.

After the addition of the acridinium-9-carboxylate aryl ester having the formula of formula I to the processed test sample, at least one basic solution is added to the test sample in order to generate a detectable signal, namely, a chemiluminescent signal. The basic solution is the same basic solution discussed previously herein, namely, a solution that contains at least one base and that has a pH greater than or equal to 10, preferably, greater than or equal to 12. As also discussed previously herein, the chemiluminescent signal generated can be detected using routine techniques known to those skilled in the art.

Figure 4:
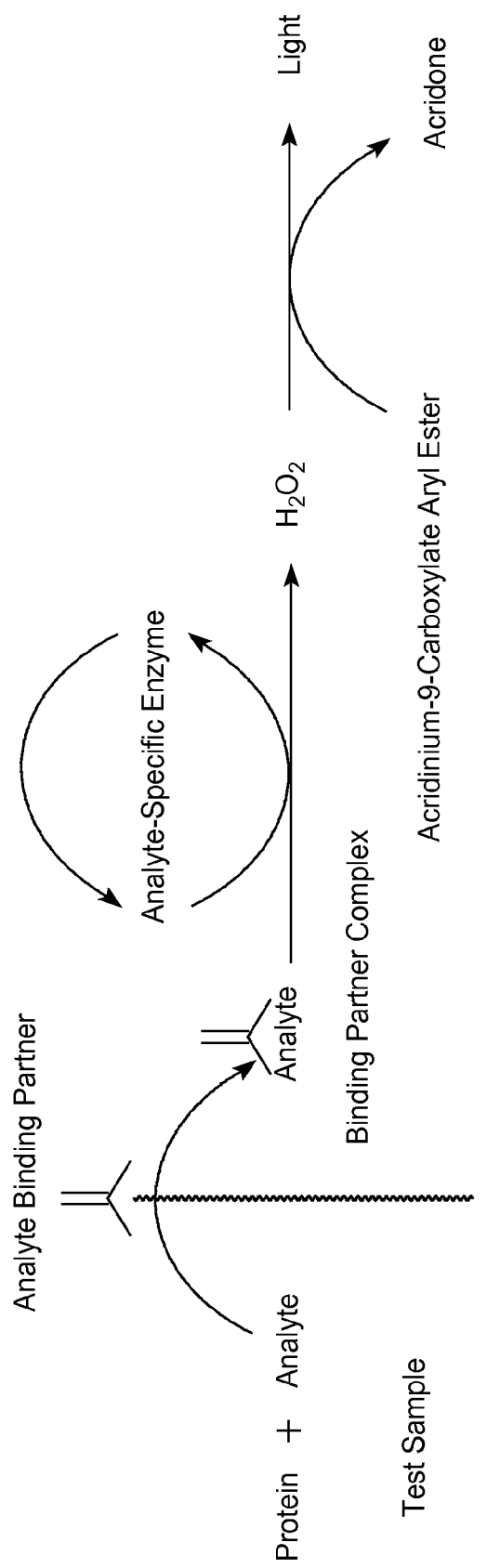
FIG. 4 is a non-limiting illustration of another aspect of the method of the present invention wherein immunoseparation techniques are used to separate the analyte from protein contained in the test sample. Specifically, an anti-analyte specific binding partner ("Analyte Binding Partner") is used. An analyte-specific enzyme which produces a peroxide, specifically, hydrogen peroxide and acridinium-9-carboxylate aryl ester are added after the analyte is separated from protein in the test sample.

In a third embodiment, the test sample contains an analyte of interest that does not contain or comprise a peroxide. However, it is preferred that for the analyte of interest to be detected that there exist one or more analyte-specific enzymes that can be added to the test sample in order to generate peroxide in the test sample, as discussed previously herein. In this embodiment, the analyte of interest is preferably, galactose, glucose, cholesterol, LDL, HDL, choline, lactic acid, uric acid, phosphatidylcholine, acetylcholine, phosphocholine, CDP-choline, lysophosphatidylcholine, triglycerides, phospholipase A2, phosholipase D, lysophosholipase D and sphingomyelin. Additionally, in this embodiment, the analyte of interest can be removed or separated from the test sample (thus removing the analyte of interest from protein contained in the test sample) using immunoseparation techniques that are well known to those skilled in the art. Specifically, in such techniques, the test sample containing the analyte of interest is contacted with a specific binding partner that binds to the analyte of interest thus forming an analyte-specific binding partner complex. In one aspect, the specific binding partner can be used in a sandwich type format (See, FIG. 4) or a competitive format, the techniques for which are well known in the art. An example of a specific binding partner that can be used is an antibody, namely, an antibody that binds to the analyte. For example, if the analyte of interest is choline, then the specific binding partner is an antibody that is capable of binding to choline. The analyte specific binding partner complex is then removed or separated from the test sample using routine techniques known in the art, such as, but not limited to, washing, thus resulting in an analyte specific binding partner complex sample.

The specific binding partner used to remove or separate the analyte of interest can be immobilized on a solid phase. The solid phase can be any material known to those of ordinary skill in the art to which the specific binding partners, such as, but not limited to, antibodies or antigens, can be attached. Examples of solid phases that can be used, include, but are not limited to, a test well in a microtiter plate, nitrocellulose, nylon, a bead or a disc (which can be made out of glass, fiberglass, latex, plastic or a paper material), a gel (for example, a gel through which the polypeptides have been run and which is subsequently dried) or a strip, disc or sheet (which can be made out of nitrocellulose, nylon, plastic or paper). The specific binding partner can be bound to the solid phase by adsorption, by covalent bonding using a chemical coupling agent or by other means known in the art, provided that such binding does not interfere with the ability of the specific binding partner to bind to the analyte of interest. Moreover, if necessary, the solid phase can be derivatized to allow reactivity with various functional groups on any of the specific binding partner. Such derivatization requires the use of certain coupling agents such as, but not limited to, maleic anhydride, N-hydroxysuccinimide and 1-ethyl-3-(3-dimethylaminopropyl)carbodiimide.

At least one analyte-specific enzyme, such as at least one dismutase, dehydrogenase, oxidase, reductase or synthase or a combination of at least one dismutase, dehydrogenase, oxidase, reductase or synthase (See, Table 1), is added to the at least one analyte-specific binding partner complex sample. The time at which the at least one analyte-specific enzyme is added to the at least one analyte specific binding partner complex sample is not critical, provided that it is added before the addition of the at least one acridinium ester having the formula of formula I, which was previously discussed herein (See, FIG. 4). The amount of at least analyte-specific enzyme that can be added to the analyte specific binding partner complex sample is from about 0.0001 unit/mL to about 10,000 units/mL.

Optionally, after the generation of the peroxide, the same specific binding partner (namely, the first specific binding partner) used to remove or separate the analyte from the test sample, or a second specific binding partner (which is different from the first specific binding partner), can be used to remove the analyte specific binding partner complex from the analyte specific binding partner complex sample (thus leaving just the peroxide in the sample).

As discussed previously herein, the peroxide that is generated by the addition of the at least one analyte-specific enzyme can then be converted to an end product having a distinct chemiluminescent emission. Such an end product is produced by adding to the analyte-specific binding partner complex sample at least one acridinium ester. Preferably, the acridinium ester is an acridinium-9-carboxylate aryl ester having a formula of formula I, which was discussed previously herein.

After the addition of the acridinium-9-carboxylate aryl ester having the formula of formula I to the analyte specific binding partner complex sample (which may or may not still contain the analyte specific binding partner complex), at least one basic solution is added in order to generate a detectable signal, namely, a chemiluminescent signal. The basic solution is the same basic solution discussed previously herein, namely, a solution that contains at least one base and that has a pH greater than or equal to 10, preferably, greater than or equal to 12. As also discussed previously herein, the chemiluminescent signal generated can be detected using routine techniques known to those skilled in the art.

In a fourth embodiment, the test sample contains an analyte of interest and does not contain or comprise a peroxide. Preferably, the analytes of interest that can be detected in this embodiment are: toxins, organic compounds, DNA, RNA, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. More preferred analytes include, but are not limited to, brain natriuretic peptide (BNP) 1-32; NT-proBNP; proBNP; preproBNP; troponin I; troponin T; troponin C; human neutrophil gelatinase-associated lipocalin (hNGAL); tacrolimus; sirolimus, cyclosporine; ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 micro-globulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HbsAg); antibodies to hepatitis B core antigen, such as anti-hepatitis B core antigen IgG and IgM (Anti-HBC); human immune deficiency virus (HIV); human T-cell leukemia virus (HTLV); hepatitis B e antigen (HbeAg); antibodies to hepatitis B e antigen (Anti-Hbe); influenza virus; thyroid stimulating hormone (TSH); thyroxine (T4); total triiodothyronine (Total T3); free triiodothyronine (Free T3); carcinoembryonic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as propoxy and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyphene.

In this embodiment, the analyte of interest can be removed or separated from the test sample (thus removing the analyte of interest from protein contained in the test sample) using immunoseparation techniques, such as those described previously herein. Specifically, in such techniques, the test sample containing the analyte of interest is contacted with a specific binding partner that is conjugated to at least one substrate-specific enzyme which produces a peroxide, to form an analyte:specific binding partner conjugate complex. The substrate-specific enzyme which produces a peroxide can be selected from the group comprising of those listed in Table 1. Specifically, the at least one substrate-specific enzyme that can be used is selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, $N^6$-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof The substrate-specific enzyme can be conjugated to the specific binding partner using routine techniques known to those skilled in the art. An example of a specific binding partner that can be used is an antibody, namely, an antibody that binds to the analyte. For example, if the analyte of interest is a troponin, then the specific binding partner is an antibody that is capable of binding to a troponin. The analyte:specific binding partner conjugate complex is then removed or separated from the test sample using routine techniques known in the art, such as, but not limited to, washing, thus resulting in an analyte:specific binding partner conjugate complex sample.

In order to generate or produce at least one type of peroxide for purposes of detecting the at least one analyte of interest, at least one substrate is added to the analyte:specific binding partner conjugate complex. Any substrate that is capable of reacting with the substrate-specific enzyme in the analyte: specific binding partner conjugate complex sample to produce hydrogen peroxide can be used. Examples of substrates that can be used include, but are not limited to those listed in Table 1. Specifically, the substrate can be selected from the group consisting of: (R)-6-hydroxynicotine, S)-2-hydroxy acid, (S)-6-hydroxynicotine, 3-aci-nitropropanoate, 3-hydroxyanthranilate, (S)-2-hydroxy-2-(4-hydroxyphenyl)acetate, 6-hydroxynicotinate, abscisic aldehyde, acyl-CoA, a primary alcohol, an aldehyde, primary monoamines, diamines and histamine, a primary amine, an aromatic primary alcohol, (2-naphthyl)methanol, 3-methoxybenzyl alcohol, an aromatic aldehyde, catechol, cholesterol, choline, columbamine, cyclohexylamine, a D-amino acid, D-arabinono-1,4-lactone, D-arabinono-1,4-lactone, D-aspartate, D-glutamate, D-glutamate, dihydrosanguinarine, (S)-dihydroorotate, 5,6-dihydrouracil, N,N-dimethylglycine, mannitol, ecdysone, ethanolamine, D-galactose, β-D-glucose, glutathione, sn-glycerol 3-phosphate, glycine, glyoxylate, D-glucose, D-galactose, D-mannose, maltose, lactose, cello-biose, L-2-hydroxyphytanate, (indol-3-yl)acetaldehyde, Lactic acid, an L-amino acid, L-aspartate, L-galactono-1,4-lactone, L-glutamate, L-gulono-1,4-lactone, L-lysine, L-lysine, A long-chain-alcohol, L-pipecolate, L-sorbose, (S)-malate, methanethiol, 6-N-methyl-L-lysine, N-acetyl-D-glucosamine, N-glycolylglucosamine, N-acetylgalactosamine, N-acetylmannosamine, NAD(P)H, a nitroalkane, an N-methyl-L-amino acid, adenosine, oxalate, 1-N-acetylspermine, polyvinyl alcohol, an S-prenyl-L-cysteine, peptidyl-L-lysyl-peptide, butane-1,4-diamine, D-glucose, D-xylose, L-sor-bose, D-glucono-1,5-lactone, pyridoxamine 5'-phosphate, pyridoxine, 6-(2-amino-2-carboxyethyl)-7,8-dioxo-1,2,3,4,5,6,7,8-octahydroquinoline-2,4-dicarboxylate, pyruvate, pyruvate, reticuline, retinal, rifamycin-B, sarcosine, a secondary alcohol, sulfite, superoxide, superoxide, (S)-tetrahydroberberine, thiamine, L-tryptophan, uric acid, vanillyl alcohol, xanthine and xylitol.

The amount of substrate added to the analyte:specific binding partner conjugate complex sample is the amount necessary to generated a sufficient amount of peroxide that is detected using the acridinium esters described herein. The amount of substrate to be added can be readily determined by one of ordinary skill in the art.

Figure 5:
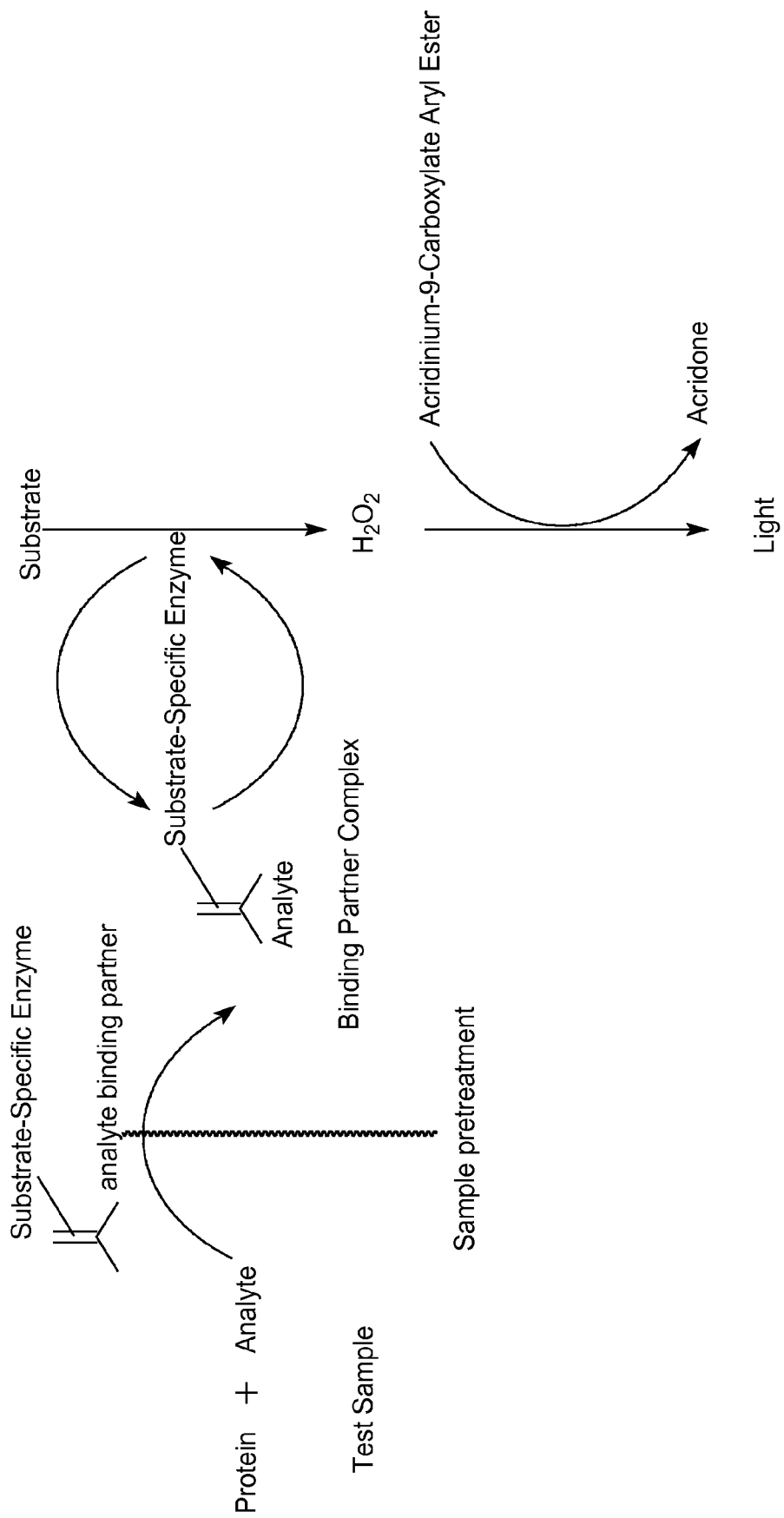
FIG. 5 is a non-limiting illustration of another aspect of the method of the present invention wherein immunoseparation techniques are used to separate the analyte from protein contained in the test sample. In this aspect, the specific binding partner ("Analyte Binding Partner") used to separate the analyte from the test sample has conjugated thereon at least one substrate-specific enzyme which produces a peroxide, specifically, hydrogen peroxide. A substrate for the substrate-specific enzyme which produces a peroxide, specifically, hydrogen peroxide and an acridinium-9-carboxylate aryl ester are added after the analyte is separated from the test sample.
Figure 6:
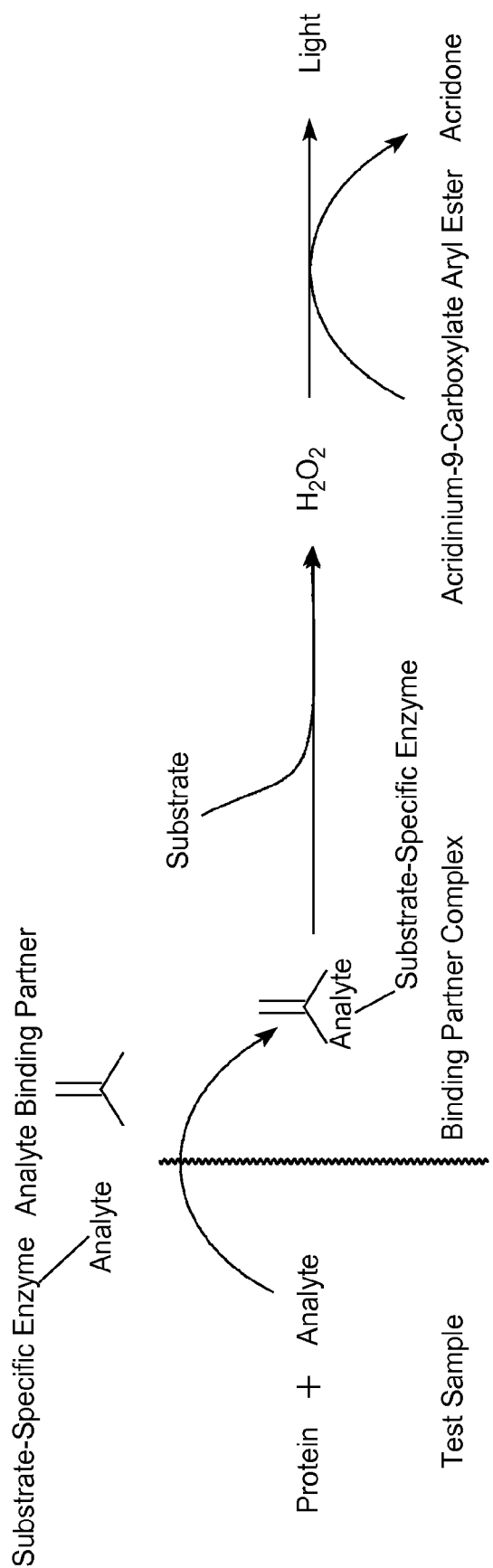
FIG. 6 is a non-limiting illustration of another aspect of the method of the present invention, similar to the method shown in FIG. 5, but in a competitive format. In this aspect, added analyte having conjugated thereon at least one substrate-specific enzyme which produces a peroxide, specifically, hydrogen peroxide, competes with the analyte of interest in the test sample for binding to the analyte-specific binding partner ("Analyte Binding Partner") to form an binding partner complex. A substrate for the substrate-specific enzyme which produces a peroxide, specifically, hydrogen peroxide and an acridinium-9-carboxylate aryl ester are added after the binding partner complex is separated from the test sample.
Figure 7:
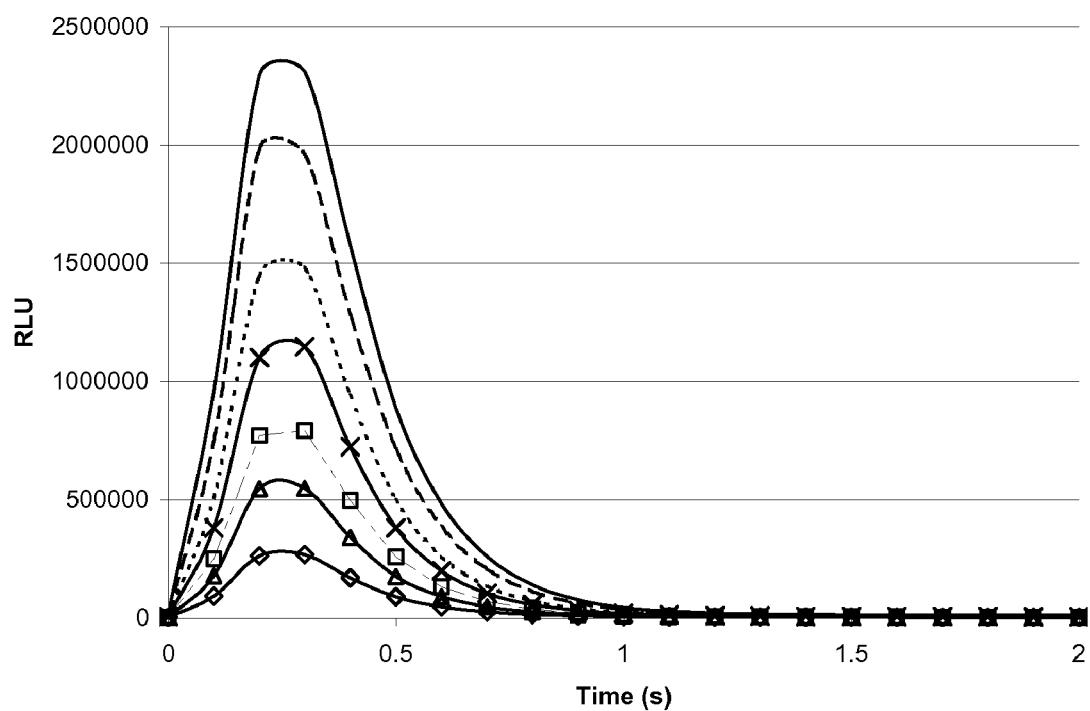
FIG. 7 shows chemiluminescence profiles for 4 µM 10-methyl-9-(phenoxycarbonyl)acridinium fluorosulfonate. Abscissa: time in seconds ("Time(s)"). Ordinate: relative light units ("RLU"). Symbols: solid line, 75 µM choline; dashed line, 50 µM choline; dotted line, 30 µM choline; -x-, 20 µM choline; -□-, 10 µM choline; -Δ-, 5 µM choline; -◇-, 0 µM choline.
Figure 8:
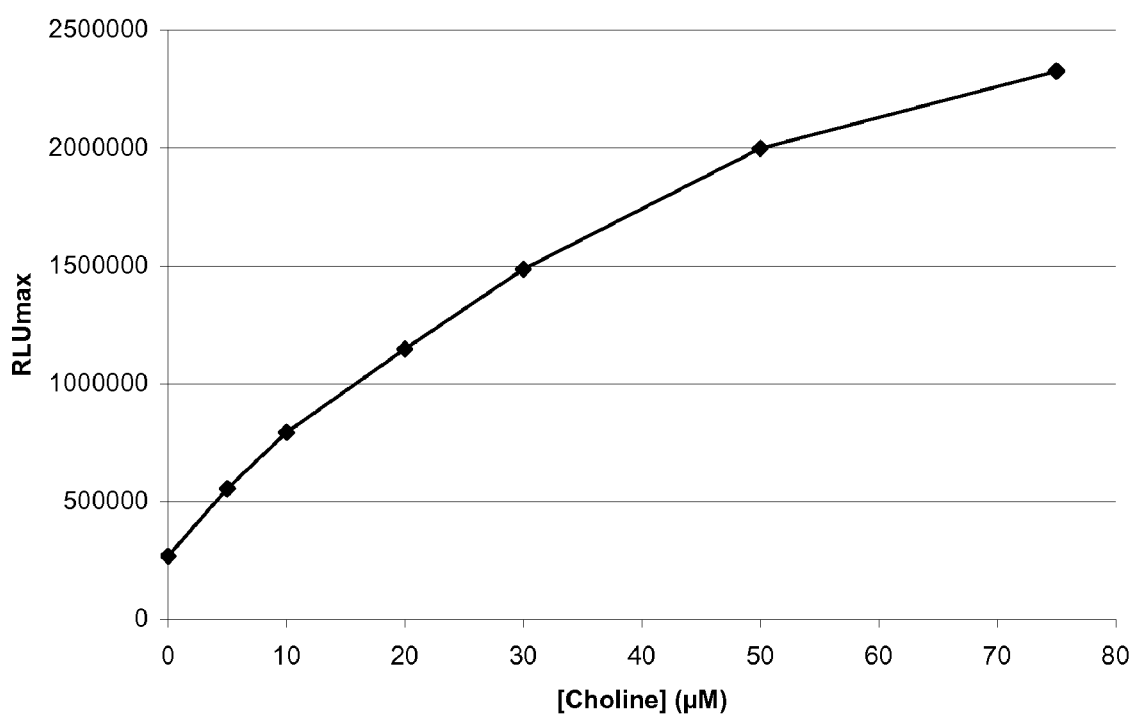
FIG. 8 shows a choline assay standard curve for 4 µM 10-methyl-9-(phenoxycarbonyl)acridinium fluorosulfonate. Abscissa: micromolar choline concentration ("[Choline] (µM)"). Ordinate: maximum relative light units ("RLUmax").
Figure 9:
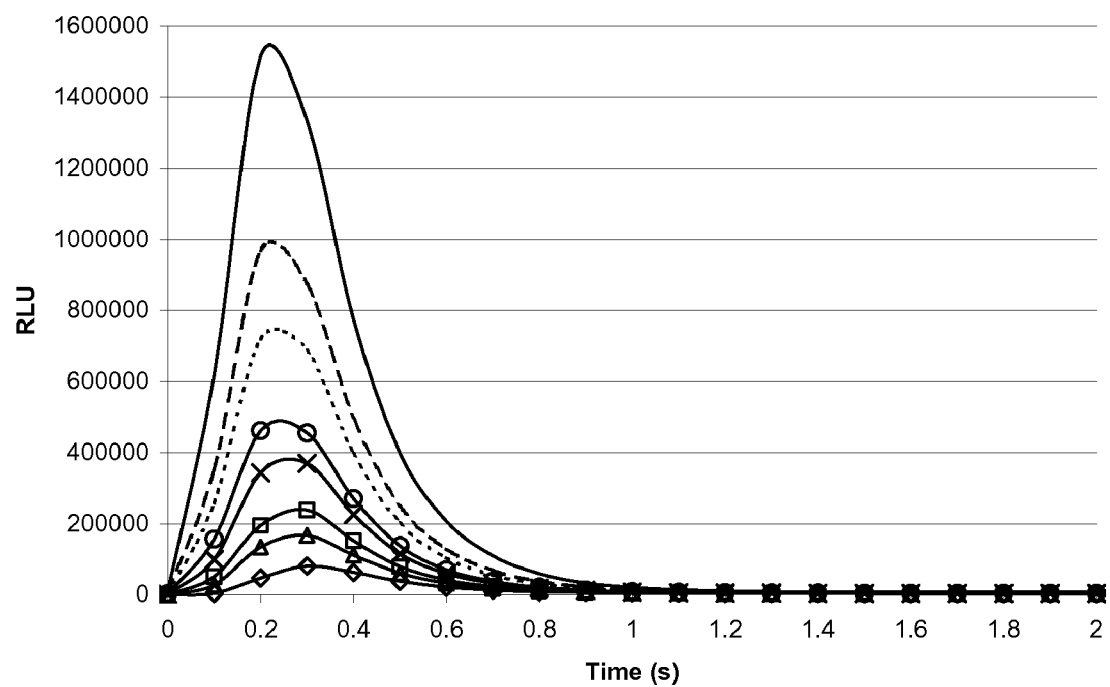
FIG. 9 shows chemiluminescence profiles for 2 µM 10-methyl-9-(phenoxycarbonyl)acridinium fluorosulfonate. Abscissa: time in seconds ("Time(s)"). Ordinate: relative light units ("RLU"). Symbols: solid line, 150 µM choline; dashed line, 75 µM choline; dotted line, 50 µM choline; -○-, 30 µM choline; -x-, 20 µM choline; -□-, 10 µM choline; -Δ-, 5 µM choline; -◇-, 0 µM choline.
Figure 10:
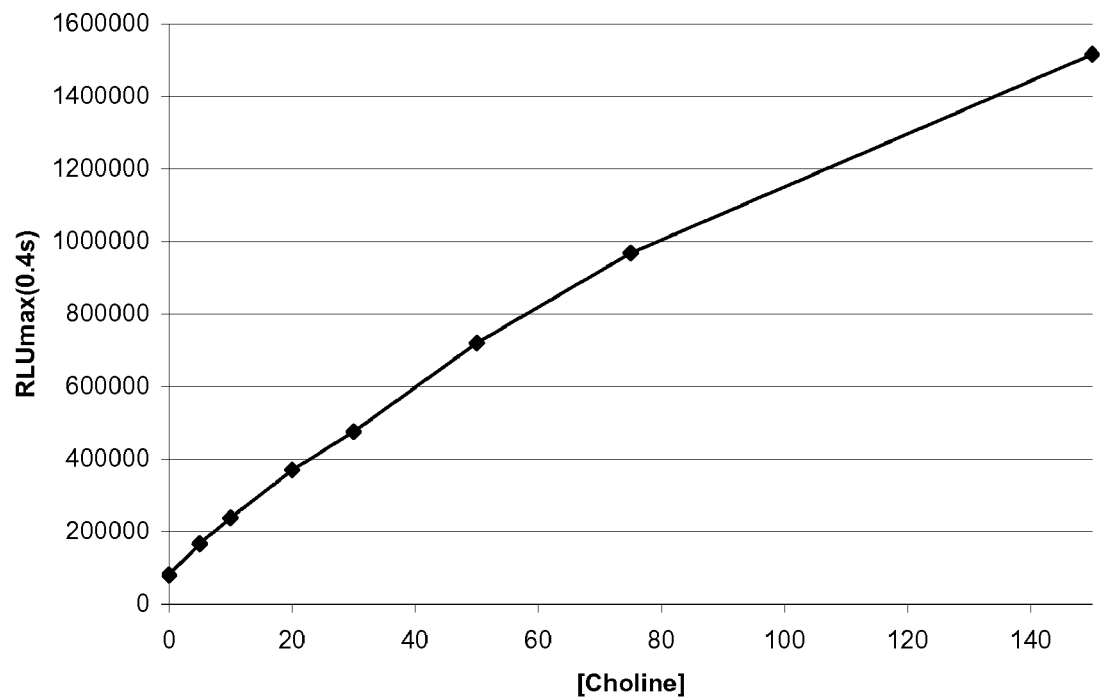
FIG. 10 shows a choline assay standard curve for 2 µM of 10-methyl-9-(phenoxycarbonyl)acridinium fluorosulfonate. Abscissa: micromolar choline concentration ("[Choline]"). Ordinate: maximum relative light units ("RLUmax (0.4 s)").

After the generation of at least one peroxide, at least one acridinium ester having the formula of formula I, which was previously discussed herein, can then be added to the analyte: specific binding partner conjugate complex sample. As discussed previously herein, the peroxide that is generated can then be converted to an end product having a distinct chemiluminescent emission. Such an end product is produced by adding to the analyte:specific binding partner conjugate complex sample at least one acridinium ester. Preferably, the acridinium ester is an acridinium-9-carboxylate aryl ester having a formula of formula I, which was discussed previously herein. This embodiment can be performed in a sandwich format (See, FIG. 5) or in a competitive format (See, FIG. 6).

After the addition of the acridinium-9-carboxylate aryl ester having the formula of formula I to the analyte:specific binding partner conjugate complex sample, at least one basic solution is added in order to generate a detectable signal, namely, a chemiluminescent signal. The basic solution is the same basic solution discussed previously herein, namely, a solution that contains at least one base and that has a pH greater than or equal to 10, preferably, greater than or equal to 12. As also discussed previously herein, the chemiluminescent signal generated can be detected using routine techniques known to those skilled in the art.

In another embodiment, the present invention relates to a kit for detecting at least one analyte in a test sample. In one aspect, the kit can contain at least one acridinium-9-carboxylate aryl ester having a formula of:

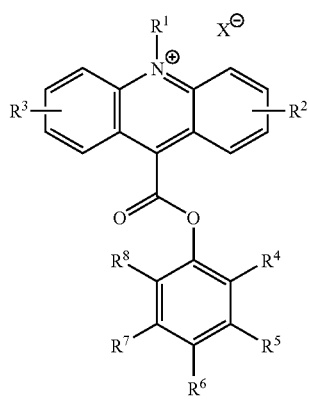

wherein $R^1$ is an alkyl, alkenyl, alkynyl, arylalkyl, aryl, sulfoalkyl or carboxyalkyl and $R^2$ through $R^8$ are each independently selected from the group consisting of: hydrogen, alkyl, amino, alkoxy, hydroxyl, carboxyl, halide, nitro, cyano, —$SO_3$, —NHC(O)R, —C(O)R, —C(O)OR, —C(O)NHR and —SCN, wherein R is an alkyl, alkenyl, alkynyl, arylalkyl, aryl, sulfoalkyl or carboxyalkyl; and X is an anion.

Additionally, the kit can contain at least one basic solution. Also, the kit can also contain one or more instructions for detecting an analyte in a test sample. Preferably, at least one of the instructions in the kit will describe the steps necessary for processing the test sample to separate or remove the analyte of interest from protein contained in the test sample. Specifically, the instructions may contain the specific protocols for separating or removing the analyte of interest from protein in the test sample. For example, the instructions may contain the specific protocols for performing ultrafiltration, extraction, precipitation, dialysis, chromatography or digestion. Alternatively, the instructions may simply refer to a publication or well-known textbook that describes the protocols for performing ultrafiltration, extraction, precipitation, dialysis, chromatography or digestion. The kit can also contain instructions for generating a standard curve for the purposes of quantifying the amount of the analyte in the test sample or a reference standard for purposes of quantifying the amount of analyte in the test sample. Optionally, the kit may also contain at least one analyte-specific enzyme, such as at least one enzyme listed in Table 1.

In another aspect, the kit can contain at least one acridinium-9-carboxylate aryl ester having a formula of:

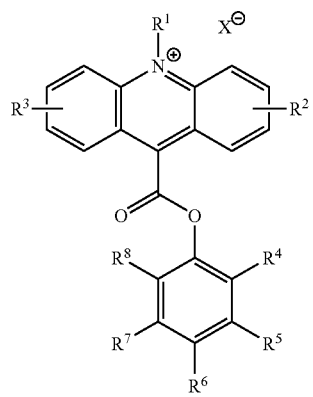

wherein $R^1$ is an alkyl, alkenyl, alkynyl, arylalkyl, aryl, sulfoalkyl or carboxyalkyl and $R^2$ through $R^8$ are each independently selected from the group consisting of: hydrogen, alkyl, amino, alkoxy, hydroxyl, carboxyl, halide, nitro, cyano, —$SO_3$, —NHC(O)R, —C(O)R, —C(O)OR, —C(O)NHR and —SCN, wherein R is an alkyl, alkenyl, alkynyl, arylalkyl, aryl, sulfoalkyl or carboxyalkyl; and X is an anion.

Additionally, the kit may also contain at least one specific binding partner. Also, the kit can contain at least one basic solution. Additionally, the kit can also contain one or more instructions for detecting an analyte in a test sample. Additionally, the kit can also contain instructions for generating a standard curve for the purposes of quantifying the amount of the analyte in the test sample or a reference standard for purposes of quantifying the amount of analyte in the test sample.

Optionally, the kit can further contain at least one enzyme listed in Table 1.

Optionally, the at least one specific binding partner contained in the kit can have conjugated thereon at least one-substrate-specific enzyme. The at least one substrate specific enzyme can be at least one enzyme listed in Table 1. If the at least one specific binding partner included in the kit has conjugated thereon at least one substrate-specific enzyme, then the kit can further contain at least one substrate. The at least one substrate that can be included in the kit includes, but is not limited to, substrates listed in Table 1.

By way of example and not of limitation, examples of the present invention shall not be given.

Example 1

Preparation of
10-Methyl-9-(Phenoxycarbonyl)Acridinium
Fluorosulfonate Stock Solution 10-Methyl-9-(phenoxycarbonyl)acridinium fluorosulfonate (Fluka Cat. No. 68617, 25 mg) was dissolved in degassed anhydrous N,N-dimethylformamide (DMF) (Aldrich Cat. No. 227056, 3 mL) to give a stock solution (20 mM). The stock solution was protected from light and stored at 4-8° C. when not in use.

Example 2

Preparation of 10-Methyl-9-(Phenoxycarbonyl)Acridinium Fluorosulfonate Working Solutions 10-Methyl-9-(phenoxycarbonyl)acridinium fluorosulfonate (20 mM in DMF) was diluted into 0.1% (wt/vol) aqueous sodium cholate (Sigma Cat. No. C6445-25), then serially diluted to a give working solutions from 250 nM-40 µM.

Example 3

Evaluation of 10-Methyl-9-(Phenoxycarbonyl)Acridinium Fluorosulfonate in an Assay for Choline Choline standards (0, 5, 10, 20, 30, 50, 75, and 150 µM in phosphate buffer, 0.2 M, pH 8) and choline oxidase (10 U/mL in phosphate buffer, 0.2 M, pH 8; 0.1% sodium cholate) were prepared as reported in Adamczyk M, Brashear R J, Mattingly P G, Tsatsos P H., Homogeneous chemiluminescent assays for free choline in human plasma and whole blood. *Anal Chim Acta.* 2006; 579(1):61-7. The assay was run a on a microplate chemiluminometer (Mithras LB-940, BERTHOLD TECHNOLOGIES U.S.A. LLC, Oak Ridge, Tenn.) equipped with three reagent injectors using 96-well black polystyrene microplates (Costar #3792). Choline standards (4 µL) were manually pipetted in quadruplicates into the wells of the microplate. Choline oxidase solution (40 µL), 10-methyl-9-(phenoxycarbonyl)acridinium fluorosulfonate working solution (40 µL) and 0.1 N aqueous sodium hydroxide (100 µL) were sequentially added and the chemiluminescent response was recorded for 2 s well by well.

The chemiluminescent response for 10-methyl-9-(phenoxycarbonyl)acridinium fluorosulfonate concentrations above 4 µM saturated the chemiluminometer detector. Typical responses for lower concentrations and the corresponding choline standard curves are shown in FIGS. 7-10.

Example 4

Figure 11:
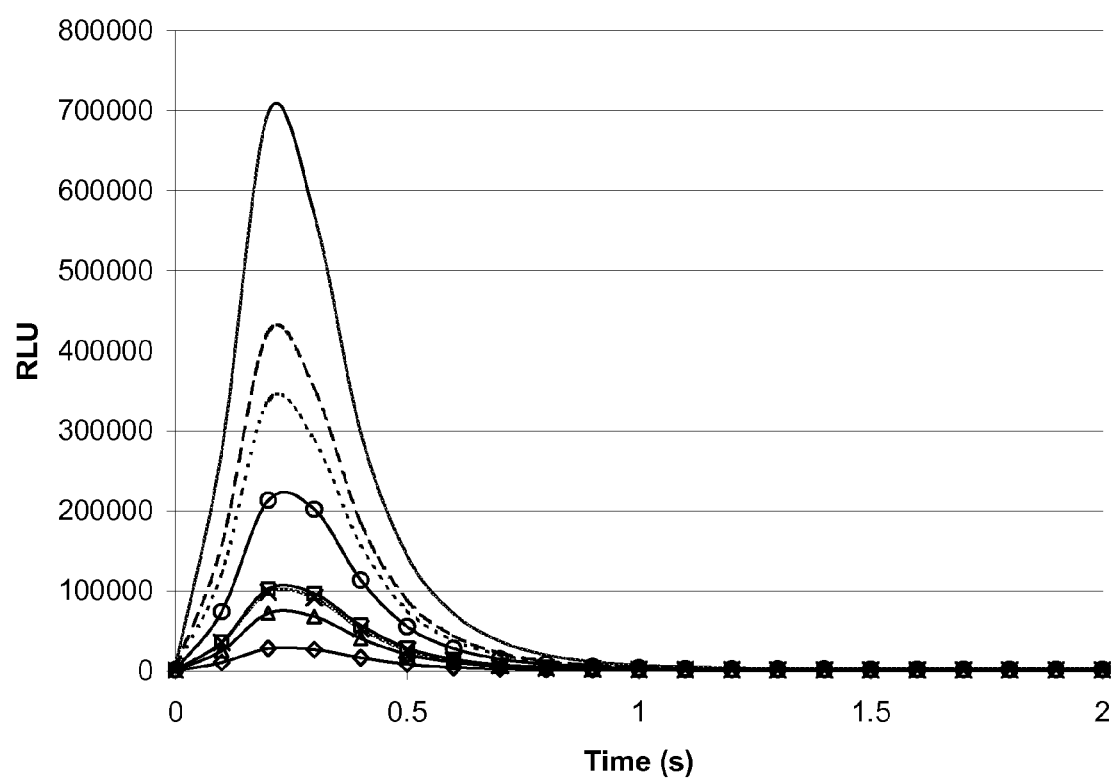
FIG. 11 shows chemiluminescence profiles of 2 µM of 10-methyl-9-(phenoxycarbonyl)acridinium fluorosulfonate after overnight storage. Abscissa: time in seconds ("Time(s)"). Ordinate: relative light units ("RLU"). Symbols: solid line, 150 µM choline; dashed line, 75 µM choline; dotted line, 50 µM choline; -○-, 30 µM choline; -x-, 20 µM choline; -□-, 10 µM choline; -Δ-, 5 µM choline; -◇-, 0 µM choline.
Figure 12:
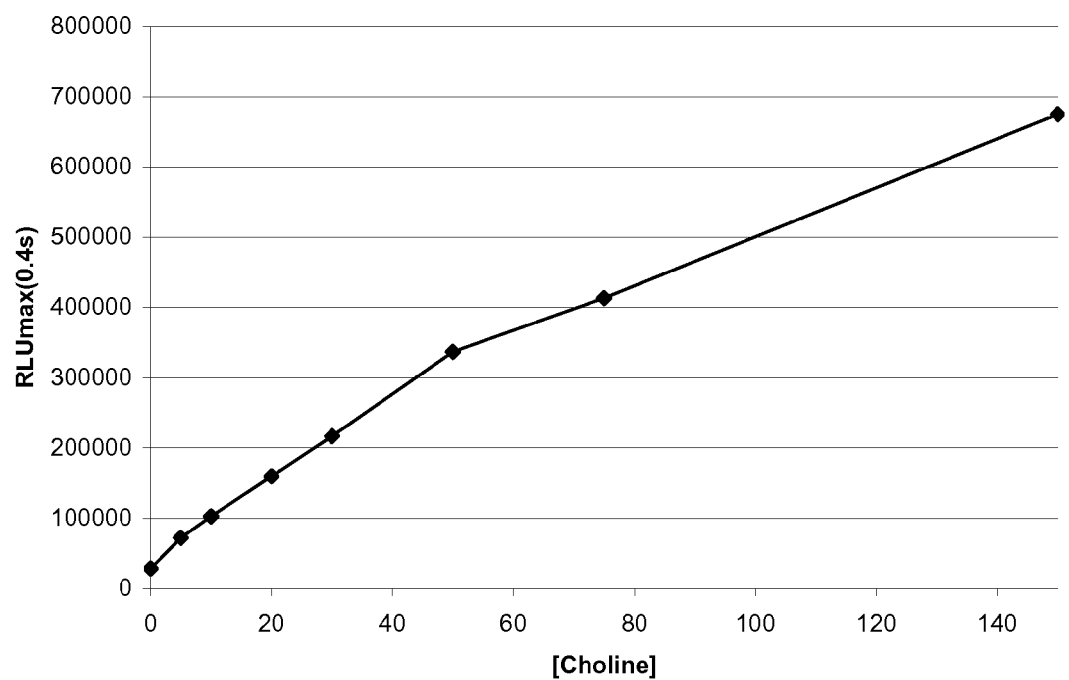
FIG. 12 shows a choline assay standard curve for 2 µM of 10-methyl-9-(phenoxycarbonyl)acridinium fluorosulfonate after overnight storage. Abscissa: micromolar choline concentration ("[Choline]"). Ordinate: maximum relative light units ("RLUmax (0.4 s)").

Effect of Pseudobase Formation with 10-Methyl-9-(Phenoxycarbonyl)Acridinium Fluorosulfonate in an Assay for Choline The experiment in Example 3 was repeated using the 2 µM 10-methyl-9-(phenoxycarbonyl)acridinium fluorosulfonate working solution that had been stored at 2-8° C. overnight. The results shown in FIGS. 11 and 12, show that the chemiluminescent response dropped by 50% due to pseudobase formation compared to Example 3.

Example 5

Figure 14:
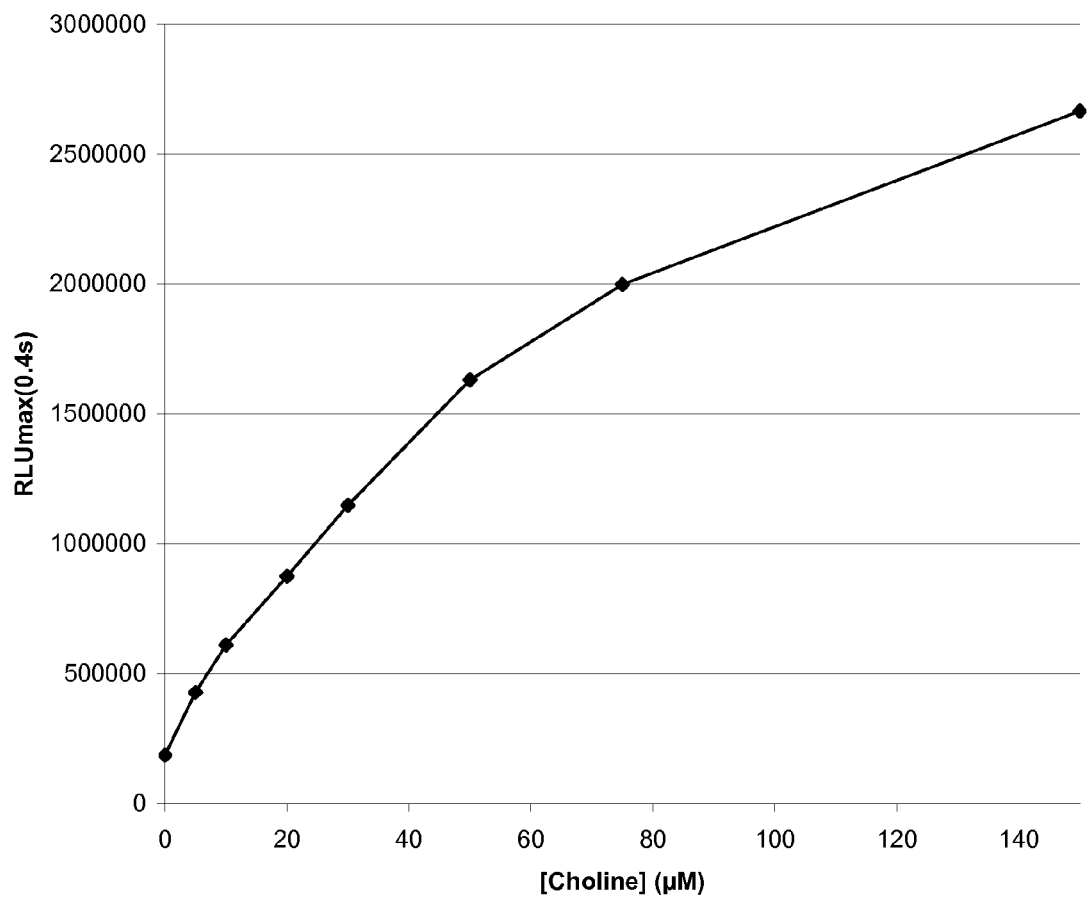
FIG. 14 shows a choline assay standard curve for 2 µM of 10-methyl-9-(phenoxycarbonyl)acridinium fluorosulfonate at pH 4. Abscissa: micromolar choline concentration ("[Choline](µM)"). Ordinate: maximum relative light units ("RLUmax (0.4 s)").
Figure 15:
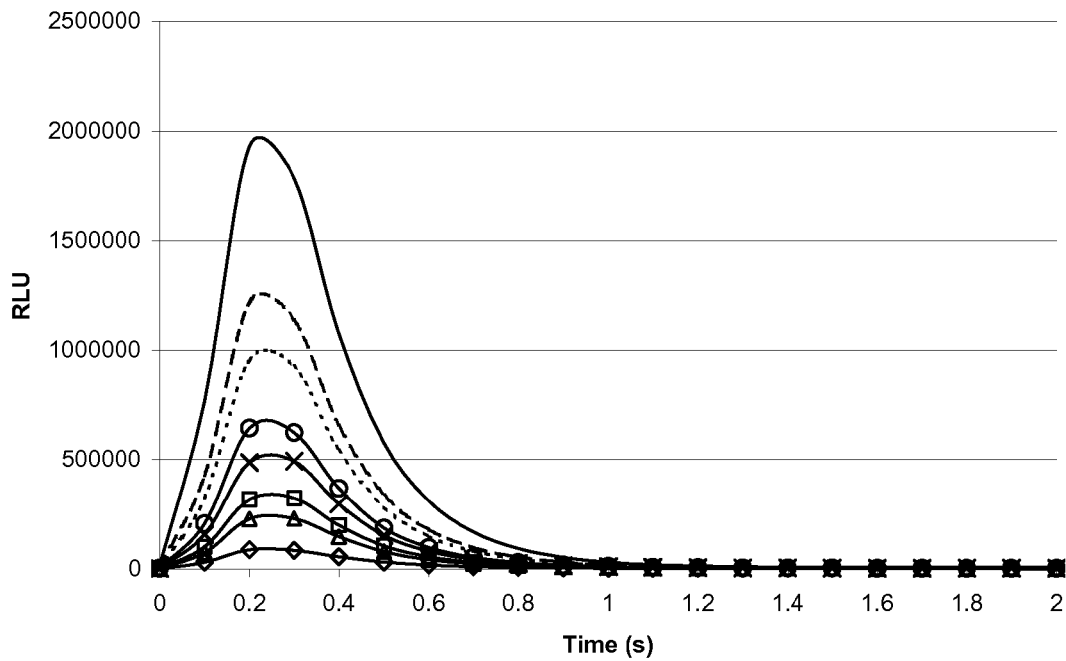
FIG. 15 shows chemiluminescence profiles for 1 µM of 10-methyl-9-(phenoxycarbonyl)acridinium fluorosulfonate at pH 4. Abscissa: time in seconds ("Time(s)"). Ordinate: relative light units ("RLU"). Symbols: solid line, 150 µM choline; dashed line, 75 µM choline; dotted line, 50 µM choline; -○-, 30 µM choline; -x-, 20 µM choline; -□-, 10 µM choline; -Δ-, 5 µM choline; -◇-, 0 µM choline.
Figure 16:
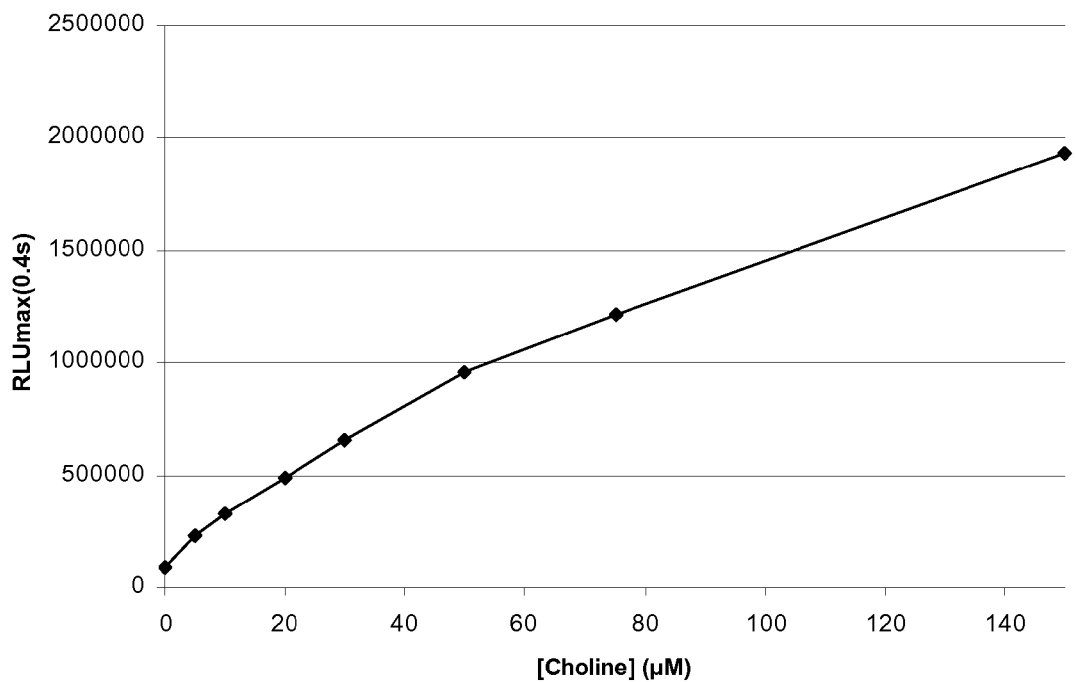
FIG. 16 shows a choline assay standard curve for 1 µM of 10-methyl-9-(phenoxycarbonyl)acridinium fluorosulfonate at pH 4. Abscissa: micromolar choline concentration ("[Choline](µM)"). Ordinate: maximum relative light units ("RLUmax (0.4 s)").
Figure 17:
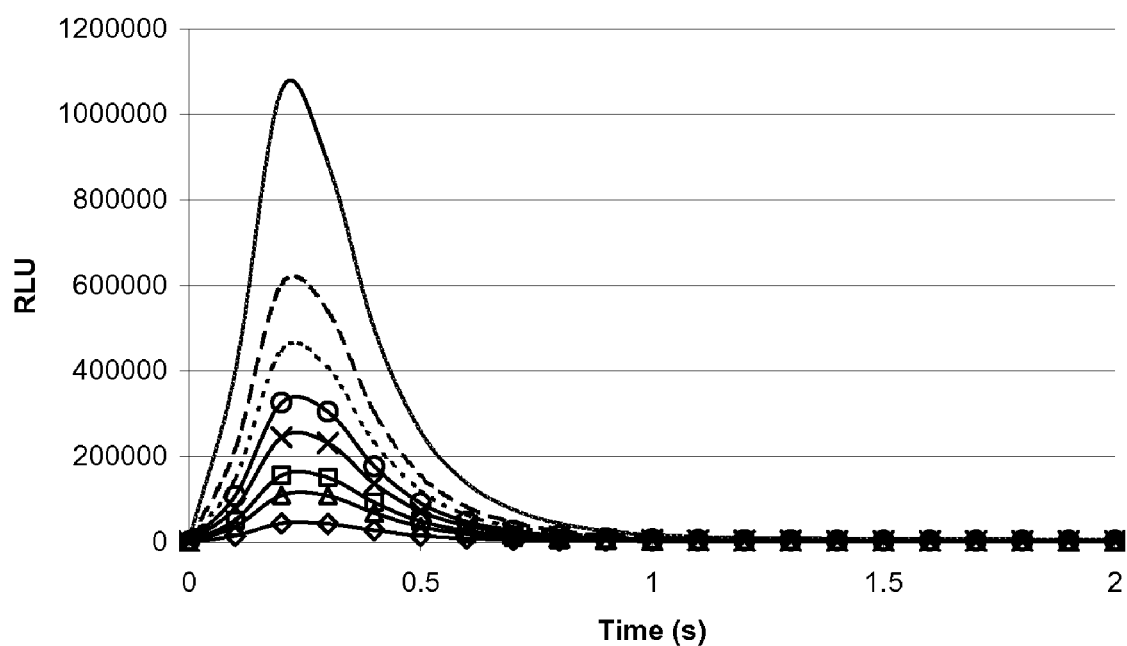
FIG. 17 shows chemiluminescence profiles for 500 nM of 10-methyl-9-(phenoxycarbonyl)acridinium fluorosulfonate at pH 4. Abscissa: time in seconds ("Time(s)"). Ordinate: relative light units ("RLU"). Symbols: solid line, 150 µM choline; dashed line, 75 µM choline; dotted line, 50 µM choline; -○-, 30 µM choline; -x-, 20 µM choline; -□-, 10 µM choline; -Δ-, 5 µM choline; -◇-, 0 µM choline.
Figure 18:
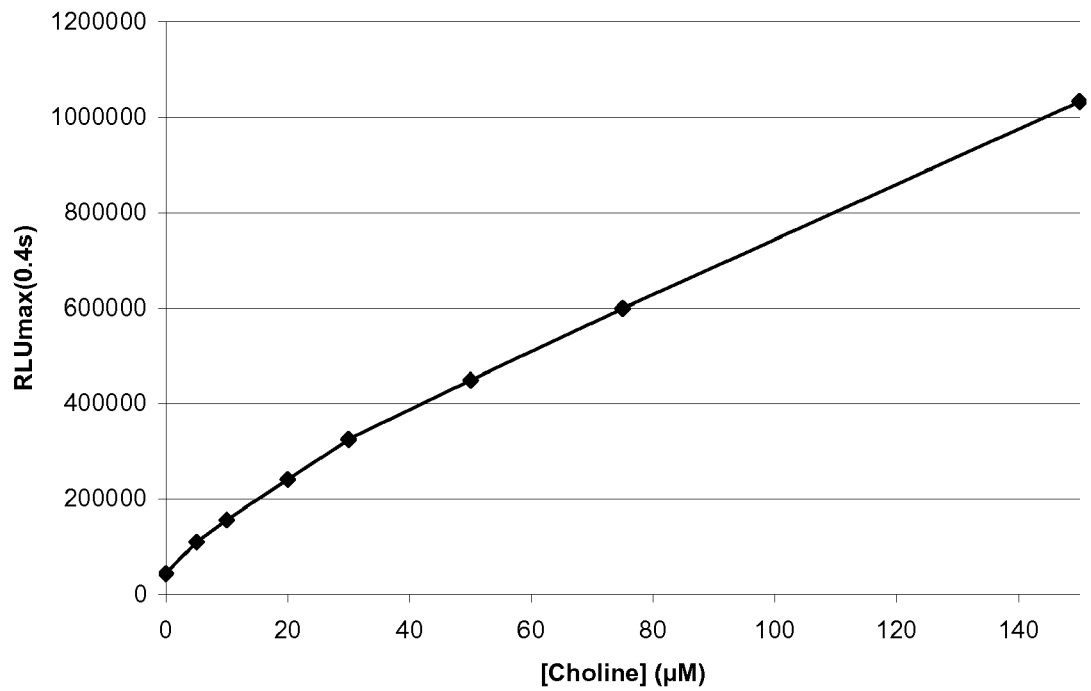
FIG. 18 shows a choline assay standard Curve for 500 nM of 10-methyl-9-(phenoxycarbonyl)acridinium fluorosulfonate at pH 4. Abscissa: micromolar choline concentration ("[Choline](µM)"). Ordinate: maximum relative light units ("RLUmax (0.4 s)").
Figure 19:
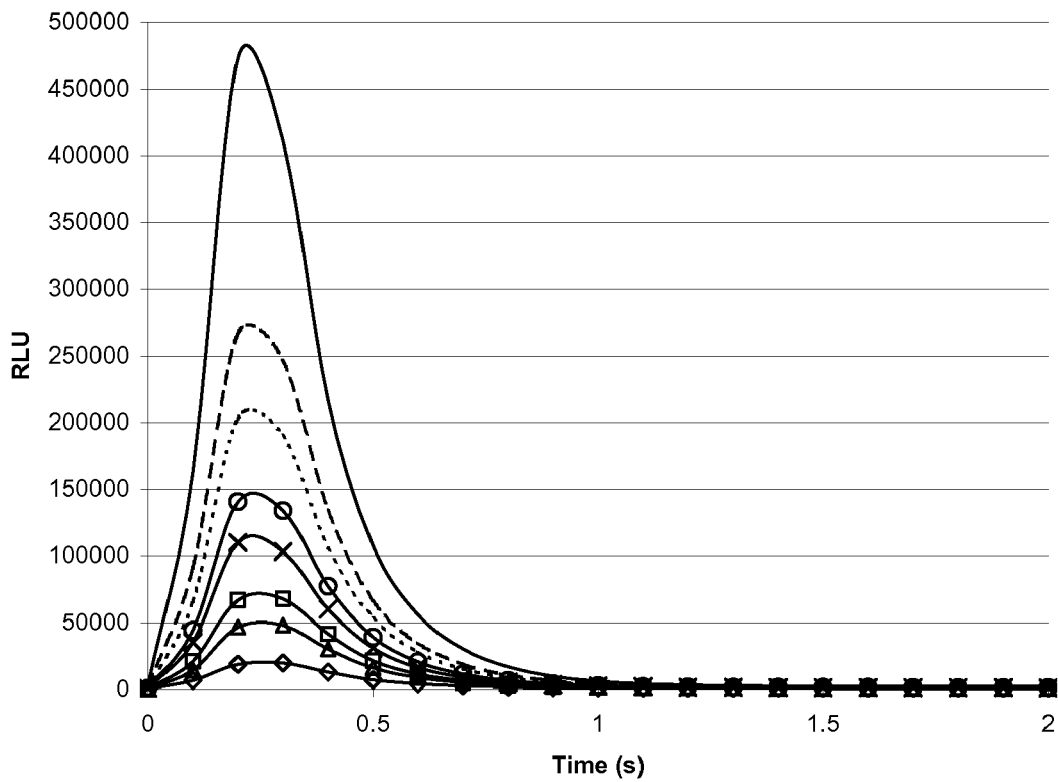
FIG. 19 shows chemiluminescence profiles for 250 nM of 10-methyl-9-(phenoxycarbonyl)acridinium fluorosulfonate at pH 4. Abscissa: time in seconds ("Time(s)"). Ordinate: relative light units ("RLU"). Symbols: solid line, 150 µM choline; dashed line, 75 µM choline; dotted line, 50 µM choline; -○-, 30 µM choline; -x-, 20 µM choline; -□-, 10 µM choline; -Δ-, 5 µM choline; -◇-, 0 µM choline.
Figure 20:
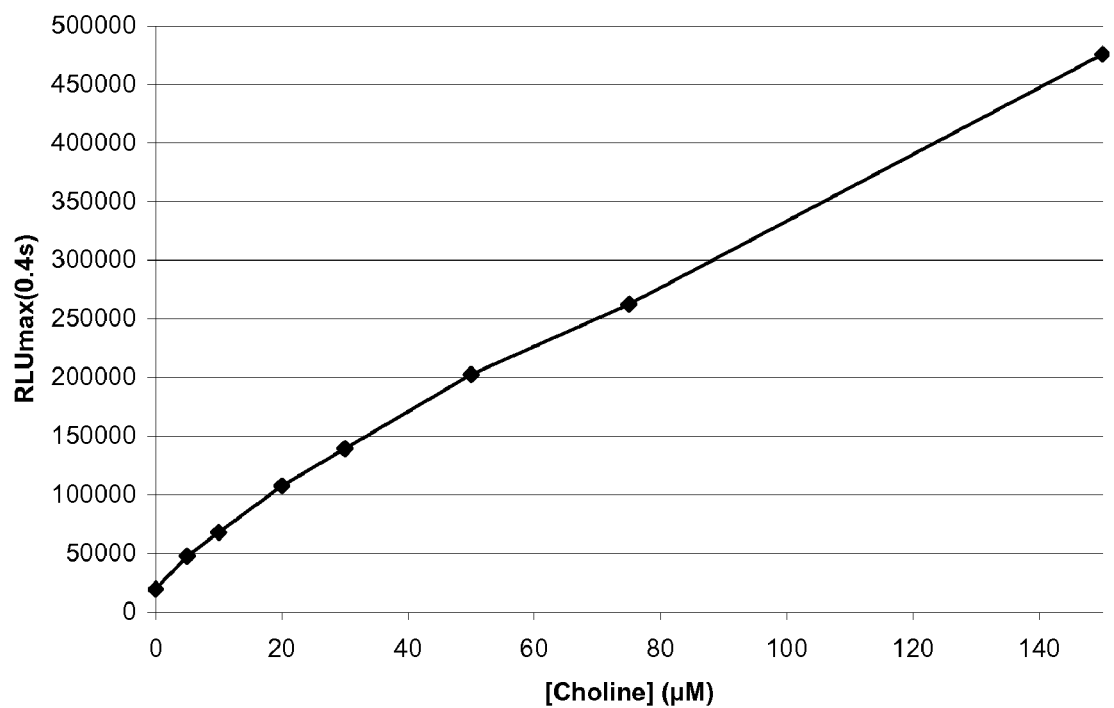
FIG. 20 shows a choline assay standard curve for 250 nM 10-methyl-9-(phenoxycarbonyl)acridinium fluorosulfonate at pH 4. Abscissa: micromolar choline concentration ("[Choline](µM)"). Ordinate: maximum relative light units ("RLUmax (0.4 s)").

Recovery from Pseudobase Formation with 10-Methyl-9-(Phenoxycarbonyl)Acridinium Fluorosulfonate in an Assay for Choline The experiment from Example 4 was repeated after acidification of the 2 µM 10-methyl-9-(phenoxycarbonyl)acridinium fluorosulfonate working solution to pH 4 with 0.1 N aqueous nitric acid. The chemiluminescent signal (FIGS. 13 and 14) was more intense than that recorded for initially for the solution on day 1 (Example 3), indicating that pseudobase formation is problematic in neutral solutions.

FIGS. 13-20 show the subsequent response of lower concentrations of 10-methyl-9-(phenoxycarbonyl)acridinium fluorosulfonate in pH 4, 0.1% sodium cholate in the choline assay.

Example 6

Assay of Plasma Samples for Choline using 10-Methyl-9-(Phenoxycarbonyl)Acridinium Fluorosulfonate without Sample Pretreatment Plasma sample A containing greater than 150 µM choline, a low plasma pool (LP) containing 14 µM choline and high plasma pool (HP) containing 40 µM were analyzed as in Example 3 using 250 nM 10-Methyl-9-(phenoxycarbonyl) acridinium fluorosulfonate, pH 4. While a normal standard curve (See, FIG. 20) was generated, the concentration of choline in the plasma samples was calculated to be less than 2 µM in all the samples.

Example 7

Assay of Plasma Samples for Choline using 10-Methyl-9-(Phenoxycarbonyl)Acridinium Fluorosulfonate with Sample Pretreatment The experiment of Example 6 was repeated using the same plasma samples that were pretreated by ultrafiltration using a Nanosep 10K Omega microtube ultrafiltration device (Pall, Cat. No. OD0101C35). The plasma sample (100 µL) was added to the device and centrifuged for 5-15 min. The ultrafiltrate was then analyzed. The reported concentration of choline in each sample read correctly, i.e., sample A (169 µM), LP (14.62 µM) and HP (41.37 µM).

Example 8

Comparison of Chemiluminescent Response in an Assay for Choline using 9-[[(3-Carboxypropyl)[(4-methylphenyl)sulfonyl]amino]-carbonyl]-10-(3-sulfopropyl)acridinium Inner Salt Choline standards were analyzed following the procedure in Adamczyk, et al. (Adamczyk M, Brashear R J, Mattingly P G, Tsatsos P H. Homogeneous chemiluminescent assays for free choline in human plasma and whole blood. *Anal Chim Acta.* 2006; 579(1):61-7). The chemiluminescence profiles at each choline concentration are shown in FIG. 21. In comparison to 10-Methyl-9-(Phenoxycarbonyl)Acridinium Fluorosulfonate at 2 µM concentration (See, FIG. 13), the instant example had a lower response (56%) at double the concentration.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of detecting an analyte in a test sample, the method comprising the steps of:
   (a) contacting the test sample containing the analyte with a specific binding partner to form an analyte specific binding partner complex;
   (b) separating the analyte specific binding partner complex from the test sample to form an analyte specific binding partner complex sample;
   (c) adding at least one analyte-specific enzyme to the analyte specific binding partner complex sample to produce peroxide;
   (d) adding an acridinium-9-carboxylate aryl ester to the analyte specific binding partner complex sample, the acridinium-9-carboxylate aryl ester having a formula of:

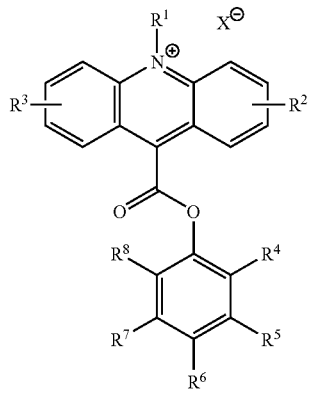

wherein $R^1$ is an alkyl, alkenyl, alkynyl, arylalkyl, aryl, sulfoalkyl or carboxyalkyl and $R^2$ through $R^8$ are each independently selected from the group consisting of: hydrogen, alkyl, amino, alkoxy, hydroxyl, carboxyl, halide, nitro, cyano, —$SO_3$, —NHC(O)R, —C(O)R, —C(O)OR, —C(O)NHR and —SCN, wherein R is an alkyl, alkenyl, alkynyl, arylalkyl, aryl, sulfoalkyl or carboxyalkyl; and X is an anion;
   (e) adding a basic solution to the analyte specific binding partner complex sample to generate a light signal, wherein the light signal is generated in a basic solution with a pH greater than or equal to 10; and
   (f) quantifying the amount of analyte in the analyte specific binding partner complex sample by relating the amount of light generated in the test sample by comparison to a standard curve for said analyte.

2. The method of claim 1, wherein the analyte-specific enzyme is selected from the group consisting of: dismutase, dehydrogenase, oxidase, reductase, synthase and combinations thereof.

3. The method of claim 2, wherein the analyte-specific enzyme is selected from the group consisting of: (R)-6-hydroxynictotine oxidase, (S)-2-hydroxy acid oxidase, (S)-6-hdyroxynicotine oxidase, 3-aci-nitropropanoate oxidase, 3-hydroxyanthranilate oxidase, 4-hydroxymandelate oxidase, 6-hydroxynictonate dehydrogenase, abscisic-aldehyde oxidase, acyl-CoA oxidase, alcohol oxidase, aldehyde oxidase, amine oxidase, amine oxidase (copper containing), amine oxidase (flavin-containing), aryl-alcohol oxidase, aryl-adehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-aspartate oxidase, D-glutamate oxidase, D-glutamate(-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, $N^6$-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenyl-cysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), retriculine oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

4. The method of claim 1, wherein the specific binding partner is an antibody that binds to the analyte.

5. The method of claim 1, wherein the basic solution has a pH greater than or equal to 12.

6. The method of claim 1, wherein the standard curve is generated from solutions of the analyte of a known concentration.

7. The method of claim 1, wherein the test sample is whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid or semen.

8. The method of claim 1, wherein the analyte is selected from the group consisting of: galactose, glucose, cholesterol, LDL, HDL, choline, lactic acid, uric acid, phophatidylcholine, acetylcholine, phosphocholine, CDP-choline, lysophophatidylcholine, triglycerides, phospholipase A2, phospholipase D, lysophospholipase D and sphingomyelin.

* * * * *